United States Patent
Vorlop et al.

(10) Patent No.: US 10,329,536 B2
(45) Date of Patent: Jun. 25, 2019

(54) METHODS FOR PRODUCING AN ACTIVE CONSTITUENT OF A PHARMACEUTICAL OR A DIAGNOSTIC AGENT IN AN MDCK CELL SUSPENSION CULTURE

(75) Inventors: Jürgen Vorlop, Marburg (DE); Christian Frech, Mannheim (DE); Holger Lübben, Wetter (DE); Jens-Peter Gregersen, Wetter (DE)

(73) Assignee: Seqirus UK Limited, Berkshire (GB)

( * ) Notice: Subject to any disclaimer, the term of this patent is extended or adjusted under 35 U.S.C. 154(b) by 177 days.

(21) Appl. No.: 10/487,707

(22) PCT Filed: Sep. 11, 2002

(86) PCT No.: PCT/EP02/10208
§ 371 (c)(1),
(2), (4) Date: Jan. 18, 2005

(87) PCT Pub. No.: WO03/023021
PCT Pub. Date: Mar. 20, 2003

(65) Prior Publication Data
US 2005/0118140 A1    Jun. 2, 2005

(30) Foreign Application Priority Data
Sep. 12, 2001 (DE) .................. 101 44 906

(51) Int. Cl.
*C12N 7/00* (2006.01)
*C12N 5/00* (2006.01)
*A61K 39/00* (2006.01)

(52) U.S. Cl.
CPC .......... *C12N 7/00* (2013.01); *A61K 39/00* (2013.01); *A61K 2039/5252* (2013.01); *C12N 2710/10051* (2013.01); *C12N 2710/16651* (2013.01); *C12N 2710/16751* (2013.01); *C12N 2710/24151* (2013.01); *C12N 2720/12051* (2013.01); *C12N 2720/12351* (2013.01); *C12N 2760/16251* (2013.01); *C12N 2760/18051* (2013.01); *C12N 2760/18551* (2013.01); *C12N 2760/20151* (2013.01); *C12N 2770/24151* (2013.01); *Y02A 50/386* (2018.01); *Y02A 50/388* (2018.01); *Y02A 50/39* (2018.01); *Y02A 50/464* (2018.01); *Y02A 50/466* (2018.01)

(58) Field of Classification Search
USPC ........................................ 435/239, 350, 383
See application file for complete search history.

(56) References Cited

U.S. PATENT DOCUMENTS

| | | | |
|---|---|---|---|
| 4,064,232 A | 12/1977 | Bachmayer et al. | |
| 4,500,513 A | 2/1985 | Brown et al. | |
| 4,525,349 A | 6/1985 | Montagnon et al. | |
| 4,783,411 A | 11/1988 | Gabliks | |
| RE33,164 E | 2/1990 | Brown et al. | |
| 5,013,663 A | 5/1991 | Acree et al. | |
| 5,753,489 A | 5/1998 | Kistner et al. | |
| 5,756,341 A | 5/1998 | Kistner et al. | |
| 5,762,939 A | 6/1998 | Smith et al. | |
| 5,911,998 A | 6/1999 | Potash et al. | |
| 6,455,298 B1 | 2/2002 | Groner et al. | |
| 6,514,502 B1 | 2/2003 | Francis | |
| 6,656,720 B2 | 12/2003 | Groner et al. | |
| 8,506,966 B2 | 8/2013 | Podda et al. | |
| 2004/0223976 A1 | 11/2004 | Bianchi et al. | |
| 2006/0147477 A1 | 7/2006 | Cabezon Siliva et al. | |
| 2006/0263386 A1 | 11/2006 | Buschle et al. | |
| 2009/0220546 A1 | 9/2009 | Podda et al. | |
| 2010/0010199 A1 | 1/2010 | Tsai et al. | |
| 2010/0189741 A1 | 7/2010 | Ballou et al. | |
| 2011/0045022 A1 | 2/2011 | Tsai | |
| 2013/0004942 A1 | 1/2013 | Stohr et al. | |

FOREIGN PATENT DOCUMENTS

| | | |
|---|---|---|
| EP | 0 019 218 | 11/1980 |
| EP | 00/19218 | 11/1980 |
| EP | 0389925 | 12/1995 |
| EP | 1260581 | 11/2002 |
| EP | 0891420 | 2/2005 |
| EP | 0833933 | 9/2005 |
| GB | 1070764 | 6/1965 |
| WO | WO91/09937 | 7/1991 |

(Continued)

OTHER PUBLICATIONS

Palache et al. Immunogenicity and reactogenicity of influenza subunit vaccines produced in MDCK cells or fertilized chicken eggs 1997. The Journal of Infectious Disease vol. 176, Supplement 1, p. S20-S23.*
Johnson. Serum-Free Systems for MDBK and MDCK Epithelial Cells Jan. 2001. Sigma-Aldrich Corporation, Life Science Quarterly, vol. 2, Issue 1.*
Merten et al. The new medium MDSS2N, free of any animal protein supports cell growth and production of various viruses 1999. Cytotechnology vol. 30, p. 191-201.*
Wrin et al. Adaptation of persistent growth in the H9 cell line renders a primary isolate of human immunodeficiency virus type 1 sensitive to neutralization by vaccine sera. The Journal of Virology, Jan. 1995, vol. 69, No. 1, pp. 39-48.*

(Continued)

*Primary Examiner* — Nianxiang Zou
(74) *Attorney, Agent, or Firm* — Finnegan, Henderson, Farabow, Garrett & Dunner, LLP

(57) ABSTRACT

The present invention concerns a method for production of an active ingredient of a drug or diagnostic agent, in which
(a) MDCK cells are infected with a virus; and
(b) the MDCK cells are cultured in suspension culture on a commercial scale under conditions that permit multiplication of the viruses;
in which culturing occurs in a volume of at least 30 L. The invention also concerns a method for production of a drug or diagnostic agent in which an active ingredient is produced according to the above method and mixed with an appropriate adjuvant, auxiliary, buffer, diluent or drug carrier.

7 Claims, No Drawings

(56) References Cited

FOREIGN PATENT DOCUMENTS

| WO | WO96/15231 | 5/1996 |
|---|---|---|
| WO | WO96/15232 | 5/1996 |
| WO | WO96/37624 | 11/1996 |
| WO | WO96137624 | 11/1996 |
| WO | WO97/11093 | 3/1997 |
| WO | WO 1997037000 A1 * | 9/1997 |
| WO | WO 97/37000 | 10/1997 |
| WO | WO 97 37000 A | 10/1997 |
| WO | WO 97/37001 | 10/1997 |
| WO | WO 97 37001 A | 10/1997 |
| WO | WO-97/38094 A1 | 10/1997 |
| WO | WO-2006/100109 A1 | 9/2006 |
| WO | WO-2007/045674 A1 | 4/2007 |
| WO | WO-2008/043774 A1 | 4/2008 |
| WO | WO-2008/068631 A2 | 6/2008 |
| WO | WO-2008/128939 A1 | 10/2008 |

OTHER PUBLICATIONS

Altman et al. HIV escape: there and back again. Nature Medicine Mar. 2004 vol. 10, No. 3, p. 229-230.*
Budowsky et al. Principles of selective inactivation of viral genome. Inactivation of the infectivity of the influenza virus by the action of beta-propiolactone. Vaccine 1991, vol. 9, No. 6, p. 398-402.*
Japour et al. Standardized Peripheral Blood Mononuclear Cell Culture Assay for Determination of Drug Susceptibilities of Clinical Human Immunodeficiency Virus Type 1 Isolates. Antimicrobial Agents and Chemotherapy, May 1993, vol. 37, No. 5, p. 1095-1101.*
Scheidler et al. Inactivation of Viruses by b-Propiolactone in Human Cryo Poor Plasma and IgG Concentrates. Biologicals 1998, vol. 26, p. 135-144.*
Tonini et al. Current approaches to developing a preventative HIV vaccine. 6, No. 2, p. 155-162. Current Opinion in Investigational Drugs 2005, vol. 6, No. 2, p. 155-162.*
Kistner O et al. Development of a mammalian cell (Vero) derived candidate influenza virus vaccine. Vaccine. May-Jun. 1998;16(9-10):960-8.*
Kurtanjek Z. Optimal nonsingular control of fed-batch fermentation. Biotechnol Bioeng. Apr. 15, 1991;37(9):814-23.*
Côté J et al. Serum-free production of recombinant proteins and adenoviral vectors by 293SF-3F6 cells. Biotechnol Bioeng. Sep. 5, 1998;59(5):567-75.*
Budowsky El et al. Principles of selective inactivation of viral genome. VI. Inactivation of the infectivity of the influenza virus by the action of beta-propiolactone. Vaccine. Jun. 1991;9(6):398-402.*
Cinatl et al. Protein-free culture of Vero cells: a substrate for replication of human pathogenic viruses. Cell Biol Int. Sep. 1993;17(9):885-95.*
Shih et al. Diagnosis of respiratory tract viruses in 24 h by immunofluorescent staining of shell vial cultures containing Madin-Darby Canine Kidney (MDCK) cells. J Virol Methods. Aug. 1999;81(1-2):77-81.*
Higareda et al. Metabolic and kinetic studies of hybridomas in exponentially fed-batch cultures using T-flasks. Cytotechnology 15: 73-86, 1994.*
https://en.wikipedia.org/wiki/Fed-batch_culture. Undated.*
Xie et al. Integrated approaches to the design of media and feeding strategies for fed-batch cultures of animal cells. Trends Biotechnol. Mar. 1997;15(3):109-13.*
Xie et al. Integrated approaches to the design of media and feeding strategies for fed-batch cultures of animal cellsTrends in Biotechnology, 1997, 15(3):109-113.*
Roessler et al.: "Temperature: A simple parameter for process optimization in fed-batch cultures of recombinant Chinese hamster ovary cells."; Enzyme and Microbial Technology; vol. 18, No. 6; 1996; p. 423-427; XP002238255.

Merten et al.: "Production of influenza virus in cell cultures for vaccine preparation"; Advances in Experimental Medicine and Biology; vol. 397, 1996, pp. 141-151; XP002039317.
Alonso-Caplen, et al., Journal of Cell Biology 97: 659-668, 1983.
Almeida, Jun. D., et al., The Effect of Trypsin on the Growth of Rotavirus, J. gen. Virol. (1978), 40, 213-218.
Appleyard, G., et al., Plaque Formation by Influenza Viruses in the Presence of Trypsin, J. Gen, Virol. (1974), 25, 351-357.
Bachmayer, Intervirology, (1975) 5:260-272.
Boycott, H.D., et al., Cell Tropism of Influenza Virus Mediated by Hemagglutinin Activation at the Stage of Virus Entry, Virology, 203, 313-319 (1994).
Brands et al., Proceedings of the 3rd International Conference on Options for the Control of Influenza, Options for the Control of Influenza III, Brown et al., Eds. Elsevier Science B.V., Amsterdam (1996), 683-693.
Brown et al., Eds., Inactivated Influenza Vaccines Prepared in Cell Culture, Developments in Biological Standardization, S. Karger AG, Basel, Switzerland (1999) 98:13-21.
Brumback, B.G., et al. "Rapid Culture for Influenza Virus, Types A and B, in 96-well plates", Clinical and Diganostic Virology, 1995, 4, 251-256.
Bulletin of the World Health Organization (1995) 73:431-435.
Bulletin of the World Health Organization, 1978, vol. 56, No. 6, pp. 991-993 (abstract).
Chaloupka, I., et al., Compariative Analysis of Six European Influenza Vaccines, Eur. J. clin. Microbial. Infect. Dis., 1996, 15:121-127.
Chemistry and Biology, vol. 29, No. 7, pp. 444-445 (1991) (translated copy, pp. 1-6).
Chomel, J.J., et al., Comparison Between Three Rapid Mthods for Direct Diagnosis of Influenza and the Conventional Isolation Procedure, Biologicals (1991) 19, 287-292.
Chomel, J.J., et al., Rapid diagnosis of influenza A. Comparison with ELISA immunocapture and culture, Journal of Virological Methods, 37 (1992) 337-344.
Couch, Robert B., et al., Diagnostic Procedures for Viral, Rickettsial, and Chlamydial Infections, Chapter 25, Influenza, pp. 431-446, 1995.
Davies, Helen W., et al., The use of a continuous cell line for the isolation of influenza viruses, Bulletin of the World Health organization, 56 (6), 991-993 (1978).
Derwent Biotechnology Abstracts Accession No. 84-06431, HEESE (1984) Patent No. DE 3237313 (English Language Abstract) (full German text patent attached).
Dictionary of Biochemistry, 1st Ed., p. 975 (1984) (translated copy, 1 page).
Fields et al. Eds., Fields Virology, Second Ed., Raven Press, NY, NY (1990) 1:1092-1093.
Frank, A.L. et al., "Comparison of Different Tissue Cultures for Isolation and Quantitation of influenza and parainfluenza viruses", J of Clin Microbiology, 1979, 10(1), 32-36.
Govorkova et al., J. Virol (1996), 70(80):5519-5524.
Govorkova et al., JID (1995) 172:250-3.
Grossberg (1964) Science 144:1246-7.
Growth of VERO and MDCK cells in EX-CELL 505 serum-free medium [online]. JRH Biosciences Research Report, issued May 2000 [retrieved on Jan. 24, 2006]. Retrieved from the Internet <URL: www.jrhbio.com/Document.aspx?ID=499>.
Hayden, Frederick G., et al., Plaque Inhibition Assay for Drug Susceptibility Testing of Influenza Viruses, Antimicrobial Agents and Chemotherapy, vol. 17, No. 5, May 1980, p. 865-870.
Herrero-Uribe, et al., Replication of Influenza A and B Viruses in Human diploid Cells, J. gen. Virol. (1983), 64, 471-475.
Hougland et al., Growth 42(2): 1790188, 1978 (Abstract only cited).
Huprikar, Jayashree, et al., A simplified plaque assay for influenza viruses in Madin-Darby Kidney (MDCK) Cells, Journal of Virological Methods, 1 (1980) 117-120.
Itoh, Heihachi, et al., Effect of Trypsin on Viral Susceptibility of Vero Cell Cultures—Cercopithecus Kidney Line, japan. J. Med. Sci. Biol., 23, 227-235, 1970.
Jennings et al., Vaccine, (1984) 2:75-80.

(56) References Cited

OTHER PUBLICATIONS

Johansson, B.E., et al., Immunization with purified N1 and N2 influenza virus neuraminidases demonstrates cross-reactivity without antigenic competition, Proc. Natl. Acad. Sci. USA, vol. 91, pp. 2358-2361, Mar. 1994.
Katz, Jacqueline M., et al. Efficacy of Inactivated influenza A Virus (H3N2) Vaccines Grown in Mammalian Cells or Embryonated Eggs, J of Infectious diseases, vol. 160, No. 2, Aug. 1989, pp. 191-198.
Kaverin, Nicolai V., et al., Impairment of Multicycle Influenza Virus Growth in Vero (WHO) Cells by Loss of Trypsin Activity, Journal of Virology, Apr. 1995, vol. 69, No. 4, p. 2700-2703.
Kessler N et al, Suitability of MDCK cells grown in serum-free medium for influenza virus production, Developments in Biological Standardization, vol. 98, 1999, pp. 13-21; discussion 73-74, XP001097586, ISSN: 0301-5149.
Khan, A.S., et al., Comparison of US Inactivated Split-virus and Russian Live Attenuated, Cold-Adapted Trivalent Influenza Vaccines in Russian Schoolchildren, JID, 1996, 173 (February), pp. 453-456.
Kilbourne, E.D., Influenza, 1987, Plenum Medical Book, 89-110.
Klenk, et al., "Activation of Influenza A Viruses by Trypsin Treatment", Virology, 1975, 68, 426-439.
Klenk, Hans-Dieter, et al., Further Studies on the Activation of Influenza Virus by Proteolytic Cleavage of the Haemagglutinin, J. gen. Virol. (1977), 36, 151-161.
Kostka, Vladimir, et al., Inhibition of chymotrypsin Activity in Crystalline Trypsin Preparations, J. of Biol chem, vol. 239, No. 6, Jun. 1964, pp. 1799-1803.
Krackeler Scientific, Inc., Medium 199 (Mod.), printed Nov. 21, 2005, pp. 1-5.
Lavrentieva, I.N., et al., Characterization of the reproduction of influenza A epidemic viruses in cell cultures, Acta virol., 30: 137-142, 1986.
Lazarowitz, et al., "Enhancement of the Infectivity of influenza A and B Viruses by Proteolytic cleavage of the Hammagglutinin Polypeptide", Virology, 1975, 68, 440-454.
Lee et al., Serial Propagation of Astrovirus in Tissue Culture with the Aid of Trypsin, J. gen. Virol. (1981), 57, 421-424.
Leland, D.S. & Harmon, M.W., Lennette, E.H. ed., Laboratory Diagnosis of Viral Infections, 2nd Ed. 1992, pp. 19-20 and 526-527.
Litwin, The growth of Vero cells in suspension as cell-aggregates in serum-free media, Cytotchnology 10: 169-174, 1992.
Lyon, Jennifer A., et al., Replication of influenza A viruses in an avian macrophage cell line, J. of Gen Virology (1991), 72, 2011-2013.
Maassab, H.F., et al., Development and characterization of cold-adapted viruses for use as live virus vaccines, Vaccine, vol. 3, Dec. 1985, pp. 54-68.
Mancini, et al., "Evaluation of the 'In vitro' multiplication of influenza virus and the enzymatic influence on viral growth", Revista de Farmacia e Bioquimica da Universidade de Sao Paulo, 1993, 29(2), 89-95, English Abstract provided.
Meguro et al., J of Clin Microbiology, vol. 9, No. 2, pp. 175-179 (1979).
Merten OW et al. Production of influenza virus in serum-free mammalian cell cultures, Developments in Biological Standardization, vol. 98, 1999, pp. 23-37, discussion 73-74, XP001097587, ISSN: 0301-5149.
Merten, O.W., et al., Evaluation of the new serum-free medium (MDSS2) for the production of different biologicals: use of various cell lines, Cytotechnology 14:47-59, 1994.
Moriuchi, Hiroyuki, et al., Human Malignant melanoma Cell Line (HMV-II) for Isolation of Influenza C and Parainfluenza Viruses, J. of Clin Microbiology, Jun. 1990, vol. 28, No. 6, pp. 1147-1150.
Murphy, Brian R., et al., Use of the Enzyme-Linked Immunosorbent Assay to Detect Serum Antibody Responses of Volunteers Who Received Attenuated Influenza a Virus Vaccines, Infection and Immunity, Aug. 1980, vol. 29. No. 2, p. 342-347.
Nakamura et al., "Method of Suspension culture for MDCK Cells and Isolation of Influenza Virus in MDCK Suspension Cultured Cells", The Journal of the Japanese Association for Infectious Diseases, vol. 54, No. 6, pp. 306-312 (1980) (translated copy, pp. 1-19).
Nakamura, K., et al., Isolation of Influenza Virus by Use of MDCK Cell Suspension, J. Jpn. Assn. Infect. Dis. 53(12) 1979, (translated copy pp. 1-11.
Nakamura, K., et al., Studies on Isolation of Virus from Patients Seemingly with Influenza—Isolation of Influenza Virus by Suspending Culture of ESK Cells, Journal of the Japanese Assoc for Infectious Dieseases, vol. 60, No. 12, Dec. 20, 1986.
Nerome et al., Journal of General Virology, vol. 39, Iss 1, pp. 179-181 (1978).
Nishimura, Hidekazu, et al., A Human Melanoma Cell Line Highly Susceptible to Influenza C Virus, J. gen. Virol. (1989), 70, 1653-1661.
Orlich M. et al., "Structural variation occurring in the hemagglutinin of influenza virus A/Turkey/Oregon/71 during adaptation to different cell types", virology, 1990, 176, 531-538.
Orstavik, Ivar, Susceptibility of continuous lines of monkey kidney cells to influenza and parainfluenza viruses in the presence of trypsin, Acta path. Microbiol. Scand. Sect. B., 89: 179-183, 1991.
Palache, A.M., et al., Influenza vaccines: the effect of vaccine dose on antibody response in primed populations during the ongoing interpandemic perios—a review of the literature, Vaccine, vol. 11, Issue 9, 1993, pp. 892-908.
Perrin, et al., "An Experimental Rabies Vaccine Produced with a New BHK-21 Suspension Cell Culture Process: Use of Serum Free Medium and Perfusion—Reactor System", Vaccine, 1995, 13(13), 1244-1250.
Pridgen, C.L., "Influenza virus RNAs in the cytoplasm of chicken embryon cells treated with 3'—deoxyadenosine", J of Virology, 1976, 18(1), 356-360.
Robertson et al., Vaccine (1995) 13:1583-1588.
Rodriguez-Boulan et al. Journal of Cell Biol, 96:866-874, 1983.
Bernard, et al., Multiplication of Viruses: An Overview, Chapter 4, Fields Virology, 3rd edition, vol. 1, 1996, pp. 101-103, and 1369-1376.
Russell, P.H. , Newcastle Disease Virus and Two Influenza Viruses: Differing Effects of Acid and Temperature on the Uptake of Infectious Virus into Bovine and Canine Kidney Cell Lines, Archives of Virology, 88, 159-166 (1986).
Skibbens et al., Journal of Cell Biology, 108:821-832, 1989.
Sugawara, K., et al., Effects of Various Proteases on the Glycoprotein Composition and the Infectivity of Influenza C Virus, Archives of Virology 68, 147-151 (1981).
Tannock, et al., "Evaluation of chicken kidney and chicken embryo kidney cultures for the large-scale growth of attenuated Influenza virus master strain", Vaccine, 1985, 3(3), 333-9, Database Dialog #05806807.
Taub et al., "Alterations in Growth Requirements of Kidney Epithelial Cells in Defined medium Associated with Malignant Transformation," J. Supramolecular Structure and Cell. Biochem., 15:63-72(1981).
Tobita, et al., "Plaque Assay and Primary Isolation of Influenza A Viruses in an Established Line of Canine Kidney Cells (MDCK) in the Presence of Trypsin", Med. Microbiol. Immunol., 1975, 162, 9-14.
Tree JA et al., Comparison of large-scale mammalian cell culture systems with egg culture for the production of influenza virus A vaccine strains, Vaccine, Butterworth Scientific, vol. 19, No. 25-26, May 14, 2001, pp. 3444-3450, XP004238940, ISSN: 0264-410X.
Woods, Gail L., et al., Rapid 24-well plate centrifugation assay for detection of influenza A virus in clinical specimens, J of Virological Methods, 24 (1989), 35-42.
Yamagishi, H., et al, Infectivity assay and neutralization test for equine influenza virus in microplate cell cultures, Veterinary Microbiology, 6 (1981) 309-315.
Yamaoka et al., Arch Virol (1995) 140:937-944.
Opposition by GlaxoSmithKline Biologicals S.A. against European Patent EP 0891421B1, "Processes for the replication of influenza viruses in cell culture, and the Influenza viruses obtainable by the

(56) References Cited

OTHER PUBLICATIONS process", Statement of Opposition under Rule 55(c) EPC, filed by GlaxoSmithKline Biologicals S.A., Belgium, printed Oct. 26, 2005.
Opposition against EP0891420B1, Filing No. 97915628.8, Sanofi Pasteur, Filed Munich, Oct. 28, 2005.
Opposition against EP0891420B1, Crucell, Opp 106420, Oct. 31, 2005.
Opposition against EP0891420B1, Solvay, Printed Nov. 21, 2005.
Opposition against EP0891420B1, Akzo Nobel, Printed Nov. 21, 2005.
Opposition against EP0891420B1, Medimmune, Printed Nov. 21, 2005.
3rd party observations for European Application No. 97915627.0-2401, Reference P16828EP/HGH, Hallybone, Huw George, dated Dec. 20, 2005.
3rd party observations for European Application No. 97915627.0-2401, Reference P16828EP/HGH, Hallybone, Huw George, dated Oct. 14, 2005.
3rd party observations for European Application No. 97915627.0-2401, Mr. Ian Armitage, York House, dated Oct. 14, 2005.
$3^{rd}$ party observations for Japanese Patent Application No. 9-535089 (Ref No. PP01280.104), English translation, receive date Apr. 9, 2004.
Van der Pol, L., Microcarrier processes and technologies at DSM Biologics, obtained Aug. 4, 2004 at http://www.bmb.psu.edu/courses/biotc489/notes/subculture.htm.
ATCC data for deposited MDCK (NBL-2) cells (CCL-34), 4 pages, obtained Aug. 4, 2004 at http://www.atcc.org/SearchCatalogs/longview.cfm?view=ce,337688,CCI-34&text=mdc . . . .
Culturing and Sub-Culturing of Animal Cells, obtained Aug. 9, 2003 at http://www.bmb.psu.edu/courses/biotc489/notes/subculture.htm, 2 pages.
JCRB9029 [MDCK (NBL-2)], 3 pages, obtained Aug. 3, 2003 at http://cellbank.nihs.go/jp/celldata/jcrb9029.htm, 3 pages.
Common Cell Lines, obtained Aug. 4, 2004.
Corning Ultra Low Attachment Products—Application Report, obtained Aug. 4, 2004.
Brands, R., et al., Influenza vaccine and cell culture technology, obtained Aug. 9, 2003 at http://www.gripp.ru/fordoctors/influenza4/282.asp.
Mancini, D.A. et al., "Evaluation of the 'in vitro' multiplication of influenza virus and the enzymatic influence on viral growth," Revista de Farmacia e Bioquimica da Universidade de Sao Paulo, 29(2): 89-95 (1993) (English Abstract).
Kilbourne, E.D., "Cytopathogenesis and Cytopathology of Influenza Virus Infection of Cells in Culture," Plenum Medical Book, 89-110 (1987).
Klenk, H-D. et al., "Activation of Influenza A Viruses by Trypsin Treatment," Virology, 68: 426-439 (1975).
Johnson, T., "Serum-Free Systems for MDBK and MDCK Epithelial Cells," Sigma-Aldrich Corporation, Life Science Quarterly, vol. 2, Issue (Jan. 2001).
Hu et al., "Large-scale mammalian cell culture," Current Biology Ltd. ISSN 0958-1669, Current Opinion in Biotechnology 1997, 8:148-153.
Tree et al., "Comparison of large-scale mammalian cell culture systems with egg culture for the production of influenza virus A vaccine strains," Elsevier Science Ltd., Vaccine 19 (2001) 3444-3450.
Doroshenko et al. (2009). "Trivalent MDCK cell culture-derived influenza vaccine Optaflu (Novartis Vaccines)," Expert Rev Vaccines, 8(6):679-88.
Genzel et al. (2006). "Serum-free influenza virus production avoiding washing steps and medium exchange in large-scale microcarrier culture," Vaccine, 24(16):3261-72.
Patriarca (2007). "Use of flu cell lines for the production of influenza virus vaccines: An appraisal of technical, manufacturing and regulatory considerations," Initiative for Vaccine Research, World Health Organization, 12 pages.
Robertson et al. (1995). "Replicative advantage in tissue culture of egg-adapted influenza virus over tissue-culture derived virus: implications for vaccine manufacture," Vaccine, 13(16):1583-8.
Alymova et al. (1998). "Immunogenicity and protective efficacy in mice of influenza B virus vaccines grown in mammalian cells or embryonated chicken eggs," J Virol, 72(5):4472-7.
Chaloupka et al. (1996). "Comparative analysis of six European influenza vaccines," Eur J Clin Microbiol Infect Dis. 15(2):121-7.
EMEA, (Jan. 2002) "Cell Culture Inactivated Influenza Vaccines," 7 pages.
Govorkova et al. (1999). "Growth and immunogenicity of influenza viruses cultivated in Vero or MDCK cells and in embryonated chicken eggs," Dev Biol Stand, 98:39-51; discussion 73-4.
Govorkova et al. (1999). "Selection of receptor-binding variants of human influenza A and B viruses in baby hamster kidney cells," Virology, 262(1):31-8.
McCullers et al. (1999). "Reassortment and insertion-deletion are strategies for the evolution of influenza B viruses in nature," J Virol. 73(9):7343-8.
Novartis Press Release (Jun. 13, 2007). "Novartis Gains European Approval for Its Innovative Flu Vaccine Optflu," 3 pages.
Palese (2006). "Making better influenza virus vaccines?" Emerg Infect Dis, 12(1):61-5.
Reina et al. (1997). "Comparison of Madin-Darby canine kidney cells (MDCK) with a green monkey continuous cell line (Vero) and human lung embryonated cells (MRC-5) in the isolation of influenza A virus from nasopharyngeal aspirates by shell vial culture," J Clin Microbiol, 35(7):1900-1.
Robertson et al. (1990). "The hemagglutinin of influenza B virus present in clinical material is a single species identical to that of mammalian cell-grown virus," Virology, 179(1):35-40.
Rocha et al. (1993). "Comparison of 10 influenza A (H1 N1 and H3N2) haemagglutinin sequences obtained directly from clinical specimens to those of MDCK cell- and egg-grown viruses," J Gen Virol, 74 (Pt 11):2513-8.
Saito et al., (2004). "Antigenic alteration of influenza B virus associated with loss of a glycosylation site due to host-cell adaptation", Journal of Medical Virology 74: 336-343.
WHO (1991). "Recommended composition of influenza virus vaccines for use in the 1991-1992 season." 66(9):57-64.
WHO (Feb. 2012). "Recommended composition of influenza virus vaccines for use in the 2012-2013 northern hemisphere influenza season." 16 pages.
WHO (Feb. 2013). "Recommended composition of influenza virus vaccines for use in the 2013-2014 northern hemisphere influenza season." 21 pages.
WHO (Feb. 2014). "Recommended composition of influenza virus vaccines for use in the 2014-2015 northern hemisphere influenza season." 15 pages.
WHO Questions and Answers (Feb. 2014). "Recommended composition of influenza virus vaccines for use in the northern hemisphere 2014-15 influenza season and development of candidate vaccine viruses for pandemic preparedness." 4 pages.
Kishida et al., (2012). "Evaluation of Influenza Virus A/H3N2 and B Vaccines on the Basis of Cross-Reactivity of Postvaccination Human Serum Antibodies against Influenza Viruses A/H3N2 and B Isolated in MOCK Cells and Embryonated Hen Eggs," Clinical and Vaccine Immunology, 19(6):897-908.

\* cited by examiner

METHODS FOR PRODUCING AN ACTIVE CONSTITUENT OF A PHARMACEUTICAL OR A DIAGNOSTIC AGENT IN AN MDCK CELL SUSPENSION CULTURE

CROSS REFERENCE TO RELATED APPLICATIONS

This application is a National Stage application of co-pending PCT application PCT/EP02/10208 filed Sep. 11, 2002, which was published in German under PCT Article 21(2) on Mar. 20, 2003, which claims the benefit of German application Serial No. DE10144906.2 filed Sep. 12, 2001. These applications are incorporated herein by reference in their entireties.

FIELD OF THE INVENTION

The invention concerns methods for production of an active ingredient of a drug or diagnostic agent in which viruses are multiplied in MCDK (Mandine Darby canine kidney) cells on a commercial scale in suspension culture.

BACKGROUND OF THE INVENTION

Infectious diseases, especially viral infections, are still of major medical importance. The need to make available better methods by means of which viruses can be multiplied in culture in order to permit research on viruses and production of vaccines therefore remains unchanged. Production of vaccines, in particular, against viral infections ordinarily requires multiplication and isolation of large amounts of the corresponding virus.

Depending on the corresponding virus, different host systems and culture conditions for virus multiplication are used in the prior art. Standard host animals, embryonic chicken eggs, primary tissue cell cultures or established permanent cell lines are used as host systems (Rolle and Mayr (editors), Microbiology, Infection and Epidemic Science, 1978; Mahy (editor), Virology, A Practical Approach, 1985; Horzinek (editor), Compendium of General Virology, 1985).

Virus multiplication in embryonic chicken eggs is connected with high costs and time demands. The eggs must be incubated before infection and then tested for viability of the embryos. Only living embryos are capable of multiplying viruses. After infection with the virus being multiplied has occurred and further incubation, the embryos are finally killed. The viruses isolated from the egg are freed of contaminants and concentrated. Since multiplication of viruses in incubated eggs is not possible under strictly sterile conditions, contaminating pathogenic microorganisms must be eliminated from the isolates if these are to be available for medical or diagnostic application.

An alternative to multiplication of viruses in chicken eggs is offered by eukaryotic host cells of defined cell lines (Gregersen, J. P., Pharmazeutische Biotechnologie, Kayser and Muller (editors), 2000, pp. 257-281). Numerous cell lines, however, are not suitable for production of vaccines or similar medically useable preparations owing to persistent foreign virus contaminations or because of the absence of demonstration of freedom from viruses, unclear origin and history.

On the other hand, the Vero cells derived from the kidney cells of monkeys are a host system that is already being used in the multiplication of individual viruses (polio virus, rabies virus) for vaccine production. These cells are available in different cell banks (for example, the American Type Culture Collection, ATCC) and are also made available by the World Health Organization (WHO) from a tested cell bank for medical research.

These Vero cells are adherent lines that require support surfaces for their growth, like glass bottles, plastic culture plates or plastic flasks. Growth on so-called microcarriers occurs in a culture of corresponding cells in the fermenter, i.e., generally small plastic spheres on whose surface the cells can grow.

It is known that adherent BHK (baby hamster kidney) and adherent MDCK (Madin Darby canine kidney) cells and other cells can also actively multiply viruses, in addition to the aforementioned Vero cells, and are being used as substrate for production of pharmaceutical products or their use is being considered. In the MDCK cell line ATCC CRL34 (NBL-2), in addition to influenza viruses, the vesicular stomatitis virus, the Coxsackie virus B5 (but not B3 or B4), reovirus [sic; typo in German] types 2 and 3, adenovirus types 4 and 5, as well as vaccinia viruses have also been experimentally multiplied. All corresponding publications, however, are geared exclusively toward adherent cultures (cf. ATCC product information). However, the suspension culture is preferred for multiplication of larger cell amounts, in which only the lymphoid and many transformed cells could thus far be multiplied in this system (Lindl (editor), Cell and Tissue Culture, 2000, pp. 173 ff). An MDCK cell line that is able to grow in suspension in protein-free culture media is disclosed in WO 97/37000. Multiplication of influenza viruses using the corresponding host cells is also described.

In addition to selection of an appropriate cell or host system, the culture conditions under which a virus strain is multiplied are also of great significance for the achievement of an acceptably high yield. To maximize the yield of desired virus strains, both the host system and the culture conditions must therefore be specifically adapted in order to achieve favorable environmental conditions for the desired virus strain. In order to achieve a high yield of different virus strains, a system that creates optimal growth conditions is therefore required. Many viruses are restricted to special host systems, some of which are very inefficient with respect to virus yield. Efficient production systems are often based on adaptations of the virus population of corresponding culture systems, often using intermediate stages with other host systems and employing protein additives—mostly serum of animal or human origin.

It is also known to experienced persons that nearly all cell cultures, after initial multiplication with addition of serum or other growth factors, can be kept at least for a certain time without serum or protein additives. For example, an arbitrary cell culture can be transferred at the time of virus infection or right before harvesting to a medium without serum or protein additives and kept until harvest. This has been common practice for years in order to obtain virus material for vaccines or diagnostic tests, while avoiding or reducing foreign proteins. Vaccines and cell cultures that were kept without this practice during the infection phase with addition of serum will have greater problems in being allowed for use in humans or animals, since the serum components can scarcely be adequately eliminated (cf. WHO recommendations "Proposed requirements for measles vaccine" (Live), Requirements for Biological Substances No. 12, revised 1978).

It is also known that many viruses can only be multiplied very poorly or not at all in protein-containing media. Viruses that rely on the activity of proteolytic enzymes (proteases)

for multiplication in culture systems are involved. Since these proteases are competitively inhibited by protein addition to the media, the addition of proteins at least from the time of infection or the production phase is logically out of the question here. Examples of viruses that must ordinarily be multiplied with addition of proteases to achieve good yields without protein additives to the infection medium, if possible, are influenza viruses and rotaviruses. Other types of viruses like paramyxoviruses and reoviruses can also profit during multiplification from media that are as low in protein as possible (Ward et al. (1984), J. Clin. Microbiol. 748-753, "Efficiency of human rotavirus propagation in cell culture"). WO 96/15231 proposes cultivation of Vero and other cells in cell cultures in which a medium that gets by without the usual protein additives is to be used.

Other viruses are known to multiply poorly regardless of the medium composition and the culture conditions, for example rabies, rota-, pneumo-, or hepatitis A viruses (Provost and Hillemann, Proc. Soc. Exp. Bio. Med., 160:213-221 (1979); and Rolle and Mayr, loc. cit.).

Finally, numerous methods are known in the prior art by means of which viruses, viral expression products or other proteins can be isolated after multiplication from the medium and/or the cells (Gregersen, loc. cit.; Mahy loc. cit.; Reimer, C. et al., Journal of Virology, December 1967, pp. 1207-1216; Navarro del Canizo, A. et al., Applied Biochemistry and Biotechnology, Vol. 61, 1996, 399; Prior, C. et al., BioPharm, Oct. 1996, 22; Janson, Jan-C. and Ryden L. (editors), Protein Purification, 1997; and Deutscher, M. (editor), Methods in Enzymology, Vol. 182, 1990).

However, no methods are known in the prior art with which a number of different viruses can be multiplied in high yield on a commercial scale in a suspension culture system that is easy to handle under conditions that are required for a pharmaceutical product. The task of the present invention is therefore to offer a method and cell culture system for multiplication of viruses that are suitable for pharmaceutical and diagnostic use on a commercial scale.

BRIEF SUMMARY OF THE INVENTION

The invention therefore concerns methods for production of an active ingredient of a drug or diagnostic agent, comprising steps in which
(a) MDCK cells are infected with a virus; and
(b) the MDCK cells are cultured in suspension culture on a commercial scale under conditions that permit multiplication of the viruses;
in which culturing occurs in a volume of at least 30 L.

DETAILED DESCRIPTION OF THE INVENTION

It was now surprisingly found that certain MDCK cell lines that have the capability of growing in suspension are particularly suited for multiplication of a number of different viruses under commercial conditions. A wide variety of viruses without an ordinarily lengthy (weeks or months long) adaptation phase can be quickly replicated in these cells. The method according to the invention can be conducted without selecting special culture conditions like media, media additives or temperatures. The cells are suitable without problem for replication of a wide variety of viruses, even those that are known to be difficult to multiply, like rabies, rota-, pneumo- or hepatitis A viruses.

The invention therefore discloses new and at the same improved possibilities of producing viruses in cell culture on a commercial scale. The products obtained are particularly suited for use in the production of drugs, especially vaccines, and/or diagnostic reagents. It could surprisingly be demonstrated that the method according to the invention can find application almost unaltered for different types of viruses without being specifically adapted to them. This has the advantage that different products (viruses) can be multiplied in the same installation or in several installations of the same design and specifications. Significant cost savings are achieved by this procedure, since the same basic process makes costly validation of a new process or a new process variant unnecessary for different products. At the same time, the method according to the invention furnishes yields that are superior to the thus far known systems that were optimized at great expense. A simplified official registration of the products resulting from the process is also obtained from the mentioned advantages of the process according to the invention, since a large part of the registration file prepared and accepted for a product can be used for other products and their registration.

Multiplication of viruses occurs in a suspension culture with a volume of more than 30 L, in which methods that use a volume of more than 50 L and more than 100 L are preferred. The method according to the invention has an upper limit in terms of volume only in the sense that the absolute size of the available culture vessel is limited. In the prior art, installations, for example, stainless steel fermenters with a size of up to 5000 and 10,000 L are known. Corresponding installations can be used for the method according to the invention.

In the cells used in the method according to the invention, MDCK cells are involved which have the property of growing in suspension culture. Cell lines that can also grow in the absence of support particles in the fermenter on a commercial scale are designated by this, which, relative to other cells, have significant advantages during handling of the cultures, scale-up of the cultures and multiplication of viruses. Methods for adaptation of MDCK cells to suspension cultures are known in the prior art (WO 97/37000). The MDCK cells can originate from the cell line MDCK 33016. The cell line was deposited under the deposit number DSM ACC2219 on Jun. 7, 1995 according to the requirements of the Budapest Convention for the International Recognition of the Deposition of Microorganisms for the Purposes of Patenting in the German Collection of Micro-organisms (DSM), in Brunswick, Federal Republic of Germany, recognized as the international deposition site.

According to another embodiment of the invention, MDCK cells are used that are capable of growing both adherently and in suspension. This embodiment has the special advantage that a cell culture system and therefore a medium for development of cells from laboratory scale to commercial production can be used. Corresponding systems simplify drug registration significantly, since only the safety of an individual cell culture system needs to be checked.

The virus can have a genome from single-stranded deoxyribonucleic acid (ssDNA), double-stranded deoxyribonucleic acid (dsDNA), double-stranded ribonucleic acid (dsRNA) or single-stranded ribonucleic acid. The single-stranded ribonucleic acid molecules can then have the polarity of messenger RNA, RNA(+) or of opposite polarity RNA(−).

The virus can be any virus known in the prior art. The viruses used in the context of the method according to the invention can be obtained from different collections, like the ATCC (American Type Culture Collection) or the ECACC (European Collection of Animal Cell Cultures). Existing production strains or virus strains already premultiplied in cell culture are generally resorted to. Specific isolates can also be established but these are better suited for the corresponding application. According to one embodiment, the virus used in the method is chosen from the group consisting of: adenoviruses, ortho- and paramyxoviruses, reoviruses, picornaviruses, enteroviruses, flaviviruses, arenaviruses, herpes viruses and pox viruses. An adenovirus, polio virus, hepatitis A virus, Japanese encephalitis virus, Central European encephalitis viruses, as well as the related eastern (Russian or other) forms, dengue virus, yellow fever virus, hepatitis C virus, rubella virus, mumps virus, measles virus, respiratory syncytial virus, vaccinia virus, influenza virus, rotavirus, rhabdovirus, pneumovirus, reovirus, herpes simplex virus 1 or 2, cytomegalovirus, varicella zoster virus, canine adenovirus, Epstein-Barr virus, as well as bovine or porcine herpes viruses, like BHV-1 or pseudorabies virus can be used, in which the use of a rabies virus, rotavirus, pneumovirus or hepatitis A virus is particularly preferred.

According to another embodiment of the present invention, the genome of the virus can include a nucleic acid sequence that codes for a heterologous, functional protein with a size of at least 10 kd. Numerous vectors for expression of heterologous proteins are known in the prior art that are based on a viral genome, for example, on a herpes, vaccinia or adenovirus genome (Galler, R. et al., Braz. J. Med. Biol. Res., February 1997, 30(2):157-68; Willemse, M. J. et al., Vaccine, November 1996, 14(16):1511-6; Efstathiou, S., Minson, A. C., Br. Med. Bull., January 1995, 51(1):45-55; Hammerschmidt, W., Curr. Opin. Mol. Ther., October 2000, 2(5):532-9; Graham, Fl., Prevec, L., Mol. Biotechnol., June 1995, 3(3):207-20; Carroll, M. W., Moss, B., Curr. Opin. Biotechnol., October 1997, 8(5):573-7; Wojcik, J., Acta. Microbiol. Pol., 1995, 44(2):191-6; Ramirez, J. C. et al., J. Virol., August 2000, 74(16):7651-5; Hagen, Anna et al., Biotechnol. Prog., 1996, 12, 406-408; Huyghe, Bernard et al., Human Gene Therapy, November 1995, 6:1403-1416).

In the context of the present invention, methods for multiplication of those viruses in which the viral genome was altered by addition or substitution of sequences so that the genome codes for a heterologous functional protein with a size of at least 10 kd, i.e., not originally belonging to the virus, are also included. According to the invention, a protein is referred as a functional protein when the protein is at least capable of triggering an immune reaction against this protein. Naturally the protein can have additional biological activities in addition to immunological activity, for example, act as an enzyme or cytokine.

The viruses used in the method according to the invention can also have deletions of individual genes in the viral genome. For example, genes of a virus to be used as a vaccine that code for pathogenicity factors can be deliberately deleted. Corresponding deletions preferably include no more than 500 or 1000 nucleotides.

Naturally the virus employed by the method according to the invention can also include a complete viral genome.

Multiplication of the viruses in suspension culture can occur according to the method of the invention in the presence or absence of serum in the medium. Special advantages are obtained by the absence of serum, since these cell culture conditions significantly simplify registration of medical use of the product so produced. By dispensing with serum additions to the culture medium, costly purification steps to eliminate medium contaminations are also avoided. Improvements with respect to quality of the product are therefore also achieved and costs are avoided on this account.

A medium in which there are no additives from serum of human or animal origin is referred to as a serum-free medium in the context of the present invention.

Specific proteins that do not have an interfering effect on the culture and subsequent use can be added in defined amounts to corresponding cultures. This type of culture medium is referred to as a chemically defined medium. Selected proteins, like mitogenic peptides, insulin, transferrin or lipoproteins are added to this medium, which can be obtained from different producers known to one skilled in the art. Mitogenic peptides in the context of the present invention are preferably understood to mean plant hydrolyzates, for example, soybean protein hydrolyzate or lysates from proteins of other useful plants.

According to a particularly preferred embodiment, however, the media are fully protein-free. Protein-free is understood to mean cultures in which multiplication of the cells occurs with exclusion of proteins, growth factors, other protein additives and non-serum proteins. The cells growing in such cultures naturally contain proteins themselves.

Known serum-free media include Iscove's medium, Ultra-CHO medium (BioWhittaker) or EX-CELL (JRH Bioscience). Ordinary serum-containing media include Eagle Basal Medium (BME) or Minimum Essential Medium (MEM) (Eagle, Science, 130, 432 (1959)) or Dulbecco's Modified Eagle Medium (DMEM or EDM), which are ordinarily used with up to 10% fetal calf serum or similar additives. Protein-free media, like PF—CHO (JHR Bioscience), chemicallydefined media like ProCHO 4CDM (BioWhittaker) or SMIF 7 (Gibco/BRL Life Technologies) and mitogenic peptides like Primactone, Pepticase or HyPep™ (all from Quest International) or lactalbumin hydrolyzate (Gibco and other manufacturers) are also adequately known in the prior art. The media additives based on plant hydrolyzates have the special advantage that contamination with viruses, mycoplasma or unknown infectious agents can be ruled out.

According to a preferred embodiment of the present invention, during culturing of the infected MDCK cells, fresh medium, medium concentrate or media ingredients like amino acids, vitamins, lipid fractions or phosphates are added.

The method according to the invention can then be conducted in a perfusion system or batch system. Culture systems in which the medium is continuously supplied and withdrawn are referred to as perfusion systems. As an alternative to this, the cells can also be cultured in a batch system in which the system is run as a largely closed system without supplying medium from inoculation to harvesting.

The cell culture conditions to be used for the desired application (temperature, cell density, pH value, etc.) are variable over a very wide range owing to the suitability of the cell line employed according to the invention and can be adapted to the requirements of the application. The following information therefore merely represents guidelines.

Multiplication of MDCK cells before infection can be conducted starting from seed cultures or small culture vessels in a perfusion system using ordinary support methods like centrifugation or filtration. It has proven advantageous to exchange the culture medium during primary culture of the cells in such a system with a rate of up to three fermenter fillings per day. The MDCK cells can be multiplied under these conditions up to cell densities of $2 \times 10^7$. Control of the perfusion rate occurs during culturing preferably by means of parameters known to one skilled in the art, like cell count, glutamine, glucose or lactate content.

When a batch system is used, cell densities up to about $8\text{-}25\times10^5$ cells/mL can be reached at a temperature of 37° C. and generation time of 20 to 30 h.

Moreover, the cells can be multiplied according to the invention in a fed-batch system before infection. In the context of the present invention, a culture system is referred to as fed-batch system when the cells are initially cultured in a batch system and depletion of nutrients (or part of the nutrients) in the medium is compensated by controlled feeding of concentrated nutrients. In a fed-batch system the MDCK cells can be multiplied to a cell density of about $1\text{-}10\times10^6$.

It has also proven advantageous to adjust the pH value of the medium during multiplication of MDCK cells before infection to a value between pH 6.6 and pH 7.8 and especially between a value between pH 7.2 and pH 7.3.

Culturing of MDCK cells before infection preferably occurs at a temperature between 30 and 40° C. and especially at a temperature between 33 and 37° C. The oxygen partial pressure is adjusted during culturing before infection preferably at a value between 25 and 95% and especially at a value between 35 and 60%. The values for the oxygen partial pressure stated in the context of the invention are based on saturation of air.

It has proven advantageous for the method according to the invention that infection of MDCK cells occurs at a cell density of preferably about $8\text{-}25\times10^5$ cells/mL in the batch system or preferably about $5\text{-}20\times10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

Culturing of the MDCK cells after infection can also occur in the perfusion, batch or fed-batch system. The same culture conditions as used before can be used (temperature between 30 and 40° C., oxygen partial pressure between 5 and 100%, pH value of the medium between pH 6.6 and pH 7.8).

According to another preferred embodiment of the present invention, during culturing of the infected MDCK cells the culture medium is replaced with fresh culture medium or the culture volume is increased by adding fresh culture medium. Exchange or supplementation of the culture medium can also occur by medium concentrate or medium ingredients like amino acids, vitamins, lipid fraction, phosphates, etc. These steps can also be conducted repeatedly during culturing of the MDCK cells.

Growth of the MDCK cells is surprisingly not significantly inhibited by multiplication in many virus systems. Especially during multiplication of hepatitis A, rhabdo- and flaviviruses (CEE), a strong growth of MDCK cells and the viruses was observed during culturing.

This permits an increase in virus yield by repeated virus harvesting from the culture supernatant and especially by increasing the total culture volume and thus the cell count by adding fresh medium. Corresponding multiple harvests represent a significant advantage of the method according to the invention, since the yield of this system is significantly improved.

The methods according to the invention therefore permit for the first time multiplication of viruses and cells in a culture system over a longer period. It could be demonstrated in some examples that the cells were still viable 28 days after infection. The duration of virus and cell multiplication is therefore selectable over a broad range by the cell culture conditions (addition of medium).

Methods that include harvesting and isolation of viruses or the proteins generated by them are also furnished by the invention. During isolation of viruses or proteins, the cells are separated from the culture medium by standard methods like separation, filtration or ultrafiltration. The viruses or the proteins are then concentrated according to methods sufficiently known to those skilled in the art, like gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

The methods according to the invention make available the active ingredient of the drug or diagnostic agent and are therefore particularly suited for production of drugs, especially for production of vaccines and diagnostic agents.

Production of the drug can include multiplication and isolation of the virus or protein produced by it and mixing with an appropriate adjuvant, auxiliary, buffer, diluent and/or drug carrier. Adjuvants in the context of the present invention are understood to mean substances that increase immune response. These include hydroxides of various metals, like aluminum hydroxide, components of the bacterial cell wall, oils or saponins. The vaccines are particularly suited for prophylactic or therapeutic treatments of viral infections.

The immunogenicity and/or efficacy of the corresponding vaccines can be determined by methods known to one skilled in the art, like protective experiments with loading infection or determination of the antibody titer necessary for neutralization. Determination of the virus amount or amount of antibodies produced can occur by determination of the titer or amount of antigen according to standard methods sufficiently known to one skilled in the art, like virus titration, hemagglutination test, antigen determination or protein determination of different types.

The methods according to the invention are also suitable for production of a diagnostic composition. The compositions can include a virus obtained from the method or a protein produced by it. In combination with additives common in the prior art and detection reagents, these compositions can be used as a diagnostic test that is suitable for virus or antivirus antibody detection.

All the virus titers in the following examples were determined according to the final dilution method and statistical 50% end point determination according to Spearman-Kaerber, known to one skilled in the art (cf. Horzinek, Compendium of General Virology, $2^{nd}$ edition, 1985, Parey Verlag, pp. 22-23). Eight test cultures were infected in microtiter plates with 100 μL amounts of a virus dilution, in which dilutions of the virus material from $10^{-1}$ to $10^{-8}$ were used. Evaluation of the virus titrations occurred either microscopically by means of the cytopathic effect as test cultures or with immunological detection methods employing virus-specific antibodies. Binding of the virus-specific antibodies is made visible as immunofluorescence with fluorescein-labeled antibodies or using biotin-labeled secondary antibodies and a streptavidin/biotin/peroxidase amplifier complex, as well as a precipitatable dye (Gregersen et al., Med. Microbiol. Immunol., 177:91-100). The unit of virus titer is the culture-infectious dose 50% ($CID_{50}$). The virus-specific detection cells used for the different types of virus and, if applicable, the immunological detection methods are mentioned in the virus-specific examples.

EXAMPLES

Example 1: Handling of the Cell Culture System as a Suspension Culture in the Early Working Steps and on a Laboratory Scale MDCK cells from seed cell vials stored in liquid nitrogen were quickly thawed by immersion in a water bath and immediately diluted in culture medium (Ultra CHO with supplement, BioWhittaker, standard medium) with a cell count of about $1 \times 10^5$ cells/mL, generally about 1:100. The cells were then separated from the medium by centrifugation (10 min at 800 G), taken up in fresh medium again and poured into spinner culture bottles (100 mL working volume, Bellco or Techne). These culture lots were incubated at 37° C. on a magnetic stirrer at 50-60 rpm. Cell growth was monitored by checking the cell count. On reaching cell counts of $8 \times 10^5$ to a maximum of $1.6 \times 10^6$ cells/mL, the cultures were transferred by dilution of the cells in fresh standard medium and seeding in new spinner culture bottles from 100 to 1000 mL working volume and incubated until the maximum or desired cell densities were reached during agitation, as described above. In these cell passages, the dilution of the corresponding culture was adapted to the type of cell growth in the range between 1:4 and 1:10 so that the maximum cell count was reached, as required, within 3 to 5 days. As an alternative, this type of cell culture was tried without addition of supplements to the medium and could be maintained without problems over at least 10 passages.

Example 2: Handling of the Cell Culture System as an Adherent Culture

Established suspension cultures (cf. Example 1) were diluted in different media so that the cell count was about $1 \times 10^5$ cells/mL and then poured into a variety of cell culture vessels (see Table 1). The cell culture volumes then corresponded to the usual amounts with a corresponding culture vessel, i.e., about 4 mm culture medium over the seeding surface or about 1 mL of medium for 2.5 $cm^2$ of culture surface. The cultures were generally incubated at the temperature of 37° C. common for most cell cultures, but significant deviations of incubation temperature were also possible without noticeable loss (see Table 1). The culture systems tested, as well as the cell growth results achieved with them are shown in Table 1 and indicate that the cell system behaves roughly the same and robustly in various media and culture systems.

Monolayer cultures produced in this way were used for titration of virus harvests in microtiter plates and for culturing of viruses under microscopic control or for immunofluorescence investigation, hemadsorption tests and other virological or immunological standard methods which can be conducted better in adherent one-layer cultures than in suspension cultures. In addition, such cultures were also particularly suitable for recovering pure virus strains by plaque purification or diluting out. Finally, the adherent cultures were also used for virus multiplication on small and large scales; larger amounts preferably in roller bottles.

TABLE 1

Cell growth in various adherent culture systems.

| Cell culture system | Cell seeding ($\times 10^5$ cells/mL) | Media employed | Additives employed | Incubation[#] | Confluent culture after __ days ($8-20 \times 10^5$ cells/mL) |
|---|---|---|---|---|---|
| Plastic culture flasks | 0.8-1.0 | MEM, EDM, Opti-MEM*, Ultra CHO* | 1-5% FCS or Supp.* | 33 or 37° C. | 4-5 |
| Plastic culture flasks | 2.0 | MEM, EDM, Opti-MEM*, Ultra CHO* | 1-5% FCS or Supp.* | 33 or 37° C. | 2-3 |
| Microtiter plates | 2.0-4.0 | MEM, EDM, Opti-MEM*, Ultra CHO* | 0.5-3% FCS or Supp.* | 33 or 37° C. | 1-2 |
| Microtiter plates | 2.0-4.0 | MEM, EDM, Opti-MEM*, Ultra CHO* | 1% FCS for 1 day, then without additives | 37° C. | 1 |
| Roller bottles | 1.0 | EDM, Opti-MEM*, Ultra CHO* | 0.5-3% FCS or Supp.* | 33 or 37° C. | 4-5 |
| Roller bottles | 1.0 | EDM, Opti-MEM*, Ultra CHO* | 1% FCS or Supp.* for 3 days, then without additives | 33 or 37° C. | 5-7 |
| Spinner + microcarrier | 2.0 | BME MEM EDM | 0.5-3% FCS or Supp.* | 33 or 37° C. | 5-7 |

BME: Basal Medium Eagle; bicarbonate supplement (2-2.5% of a 5% stock solution)
MEM: Minimum Essential Medium; bicarbonate supplement (2-2.5% of a 5% stock solution)
EDM: Dulbecco's Modified Eagle Medium; bicarbonate supplement (2-2.5% of a 5% stock solution)
FCS: fetal calf serum
Supp.: Ultra CHO supplement
[#]adjusted value; the actually measured values with deviations by +2 and −3° C.
*manufacturer: Bio-Whittaker

Example 3: Virus Isolation, Recovery and Production of Seed Virus Preparations Primary isolates, like virus-containing organ, tissue or tissue fluid samples, throat swabs or stool samples were suspended in an ice bath in standard medium (any other media or phosphate buffers are likewise possible) with addition of antibiotic (PSN: 100 U/mL penicillin, 100 µg/mL streptomycin, 50 µg/mL neomycin) and homogenized, if necessary (finely ground with mortars, scalpel blades or a so-called Douncer or Potter homogenizer). The suspension obtained was filtered with an ordinary laboratory syringe filter adapter with a pore size of 0.45 µm (for isolation of smaller, uncoated viruses also 0.2 µm). The filtrate was inoculated in small culture flasks (25 cm$^2$, see Example 2) with fresh culture medium. To increase the yield several cultures were provided with an inoculum of 100 µL to 1 mL and then incubated at 37° C. For virus isolates from the upper respiratory tract, it is recommended that additional cultures be prepared at a lower incubation temperature of 33° C.

Pure virus isolates already multiplied in the culture were used for infection directly in the culture system according to the invention according to Examples 1 or 2. However, since a higher virus content of the virus preparation could be assumed here, smaller inoculum amounts of 100 µL or less were generally used. A MOI (multiplicity of infection) of 0.1 and 0.01 was preferred for such first infections in the culture system according to the invention; infection with MOIs in steps diminishing by a factor of 10 from 10 to 0.0001 was repeated when the result was unsatisfactory.

The infected cultures were then examined daily with a microscope for virus-related cell damage (CPE, cytopathic effect) and compared with control cultures. As an alternative, in viruses that cause no CPE, the culture was examined for the presence of specific virus antigens or their genes (e.g., specific HA tests depending on the type of virus; ELISA, PCR). After three to four days, or a positive finding (shrinkage of the cells, cell death, rounding and dissolution of the cell lawn in adherent cultures, plaque formation), cell-free centrifuged culture supernatants were frozen as samples, and with a negative or doubtful finding on the other hand the entire culture was adjusted with fresh medium to a cell count of $1 \times 10^5$ cells (dilution of suspension cultures or trypsin treatment of the adherent cultures with subsequent dilution of the individual cells) and further incubated distributed in new cultures. Since this corresponded in most media to a dilution of the cultures of 1:4 to 1:20, to avoid logarithmic multiplication of the number of cultures, after the second such culture passage at the latest only a part of the possible cultures were further maintained. After three to four passages, virus isolates could be successfully isolated and detected from the appropriate virus-containing starting material.

For most virus types, depending on the virus content and quality of the starting material, a virus-related CPE was found after 2 to 7 days of incubation (see also virus-specific examples). Some viruses, however, multiply very slowly or exhibit no CPE and must therefore be detected by extended passages and incubation times or specific tests (the required methods are listed under the specific virus examples). As an example for a virus without CPE with slow multiplication which also requires a special detection system, the special example of hepatitis A virus is referred to. The detection test described there is also suitable for detection of other viruses, especially those without specific CPE, when corresponding antisera are used.

Practically a newly isolated virus should only be used after three-fold plaque purification or preparation of a pure isolate by the so-called limited dilution technique. The methods required for this can be taken from specialist textbooks according to the prior art (see, e.g., B. W. Mahy: Virology—A practical approach; IRL Press, Oxford, 1985).

If appropriate virus preparations are available from the primary isolate or as an established strain, these are then used for infection of spinner cultures in order to recover a homogenous seed virus for production purposes. Without restricting ourselves to the object of the invention, a first infection is initially recommended in small spinner cultures with 100 mL culture medium with MOIs from 10 to 0.00001, preferably 0.1 to 0.0001. The most favorable conditions (especially with reference to MOIs and harvest times) to achieve more rapid and higher virus values or yields were chosen in order to produce a seed virus in a culture system of the required size in an additional virus passage, according to the prescribed production scale and number of production runs. Depending on the virus yields achieved and the production time prescribed, the scale for this seed virus passage could be from a few spinner cultures on up to a 1000 mL scale to small fermenters up to roughly 10 L of volume or more. The harvested virus was freed of any cell residues by filtration or centrifugation and aliquoted into small amounts suitable for production and stored at temperatures below −70° C., if possible.

Example 4: Handling of the System as Adherent Microcarrier Culture for Production Purposes Culturing of adherent MDCK cells occurred in roller bottles according to Example 2, Table 1 with BME plus 3% fetal calf serum (FCS). After culturing in the system, the cells were detached from the surface of roller bottles. This occurred enzymatically with an appropriate trypsin solution with ordinary methods known to one skilled in the art. As an alternative, according to Example 1, suspension cells were cultured in the spinner cultures and used directly to coat the microcarrier.

The production fermenter was filled with microcarriers of the Cytodex 3 type (Pharmacia). The microcarrier (specific weight 5 g/L) was autoclaved and conditioned with nutrient media. The method guaranteed adhesion of the cells to the surface of the microcarrier. The cells recovered in this manner were transferred to the production system so that the cell density was $1 \times 10^5$ cells/mL. The cells adhered to the microcarrier and were cultured to confluence or to achieve a cell density of $3 \times 10^6$ cells/mL.

After the cell culture phase, the nutrient medium present was replaced with fresh nutrient medium. For this purpose, protein-free nutrient media were used. Two wash cycles were run.

A wash cycle consisted of turning off the agitator, settling of the microcarrier, removal of the nutrient medium consumed, addition of fresh nutrient medium and resuspension of the microcarrier. After the washing step the cell culture was mixed with trypsin (2.5 mg/L).

Infection of the cell culture with seed virus then occurred. This seed virus was obtained and used according to Example 3. The MOI was then virus-specific and amounted to between 0.1 and 0.000001, preferably between 0.01 and 0.0001. After the end of the infection phase, whose time, on the one hand, is determined by the specific virus (see specific examples) and, on the other hand, also by the MOI chosen, the agitator was stopped and the microcarriers sedimented. The virus-containing supernatant was taken off and purified by appropriate separation methods from cell residues. For cell separations, ordinary centrifuges or separators, filters and crossflow filtration units known to one skilled in the art were used.

Example 5: Handling of the System as Suspension Culture Up to a Production Volume on a 1000 L Scale Using Serum-Free Medium Culturing of suspension cultures for a production volume of 1000 L occurred with spinner bottles (Techne Co.) on a small scale to 1000 mL culture volume (see Example 1). The cell density in the spinner was $1\times10^5$ cells/mL. The cells were cultured in the batch process and transferred at a cell density of $1\times10^6$ cells/mL by simple dilution in fresh medium in a 1:10 ratio. Serum-free medium (Ultra CHO, BioWhittaker) was used as medium for cell culture. From a volume of 10 L we used agitated fermenters (30 agitator revolutions per minute) with permanent aeration and temperature control (control temperature 37° C. for a cell culture), pH value (control range 7.1 to 7.3) and oxygen partial pressure (45 to 55% $pO_2$) (technical details as in Table 2). The scale-up volumes were 10 L, 100 L, 1000 L according to the transfer ratio of 1:10. The fermenters reached the final cell density of $1\times10^6$ cells/mL and a time of 3 to 4 days at an initial cell density $1\times10^5$ cells/mL. On a 1000 L scale, a fed-batch was additionally conducted with glucose solution (100-200 g/L) in order to increase the cell density to $3\times10^6$ cells/mL. The cell yields achieved are shown in comparison in Table 2.

Example 6: Handling of the System as Suspension Culture to Production Volumes Up to a Volume of 1000 L Using Chemically Defined Medium Culturing of the suspension cultures for a production volume of 1000 L occurred as described in Example 5. On the other hand, a chemically defined medium (ProCHO4CDM) was used as an alternative for cell culture. It proved to be advantageous to conduct three to five prepassages for adaptation in this medium. The cell yields achieved are compared in Table 2.

Example 7: Handling of the System as a Suspension Culture up to a Production Volume on a 1000 L Scale Using a Protein-Free Medium Culturing of the suspension cultures for a production volume of 1000 L occurred as described in Example 5. Protein-free medium (SMIF7, Life Technologies) was used as medium for cell culture. It proved to be advantageous to run 5-10 prepassages for adaptation in this medium. The cell yields achieved are compared in Table 2.

TABLE 2

Culturing of cells (MDCK 33016) for a production scale in a fermenter using various methods and media.

| No. | Method | Medium | N/T/pO$_2$/pH | X$_0$ | X |
|---|---|---|---|---|---|
| 1 | Batch | Ultra CHO | 30 min$^{-1}$<br>37° C.<br>45-55%<br>7.1-7.3 | $1 \times 10^5$ mL$^{-1}$ | $1 \times 10^6$ mL$^{-1}$ |
| 2 | Fed-batch | Ultra CHO | 30 min$^{-1}$<br>37° C.<br>45-55%<br>7.1-7.3 | $1 \times 10^5$ mL$^{-1}$ | $3.1 \times 10^6$ mL$^{-1}$ |
| 3 | Batch | ProCHO4CDM | 30 min$^{-1}$<br>37° C.<br>45-55%<br>7.1-7.3 | $1 \times 10^5$ mL$^{-1}$ | $1 \times 10^6$ mL$^{-1}$ |
| 4 | Fed-batch | ProCHO4CDM | 30 min$^{-1}$<br>37° C.<br>45-55%<br>7.1-7.3 | $1 \times 10^5$ mL$^{-1}$ | $3.3 \times 10^6$ mL$^{-1}$ |
| 5 | Batch | SMIF7 | 30 min$^{-1}$<br>37° C.<br>45-55%<br>7.1-7.3 | $1 \times 10^5$ mL$^{-1}$ | $1 \times 10^6$ mL$^{-1}$ |
| 6 | Fed-batch | SMIF7 | 30 min$^{-1}$<br>37° C.<br>45-55%<br>7.1-7.3 | $1 \times 10^5$ mL$^{-1}$ | $3.0 \times 10^6$ mL$^{-1}$ |

X$_0$: Initial cell density
X: Final cell density
N/T/pO$_2$/pH: Agitator speed, temperature, oxygen partial pressure, pH value

Example 8: Handling of the System in the Production Phase with Serum-Free Medium After culturing of suspension cultures to a production scale according to Example 5, the cells were distributed to three fermenters of equal volume 3×1000 L and filled with fresh medium. Each fermenter received ⅓ volume of pre-culture and ⅔ volume of fresh medium. The same medium as in the culturing phase was used (UltraCHO, BioWhittaker). After filling, the cell culture was mixed with 10 mg/L trypsin. Infection of the cell culture with a seed virus (influenza B/Harbin/7/94) then occurred at a MOI of 0.001 and further incubation under the same fermentation conditions as during cell culture, but at 33° C., over 96 h. The cell-containing supernatant was then taken off and the cells then separated with a separator. An additional filtration step occurred through a cartridge filter with a pore size of 0.45 µm to separate additional fine particles.

The virus harvests were tested for virus content with standard methods in the HA test with 0.5% chicken erythrocytes and by virus titration in adherent MDCK cells: the measured HA content was 1024 U, the virus titer was $10^{8.2}$ $CID_{50}/mL$.

Example 9: Handling of the System in the Production Phase with Chemically Defined Media Preparation of the production cells occurred as described in Example 8. However, chemically defined medium (ProCHO4CDM, BioWhittaker) was used as fresh medium. After filling, the cell culture was mixed with 2.5 mg/L trypsin. Subsequent infection was conducted as described in Example 8.

The measured HA content was 1024 U, the virus titer was $10^{7.5}$ $CID_{50}/mL$.

Example 10: Handling of the System in the Production Phase with Protein-Free Medium Preparation of the production cells occurred as described in Example 8. However, protein-free medium (SMIF7, Life Technologies) was used as fresh medium. After filling, the cell culture was mixed with 2.5 mg/L trypsin.

Subsequent infection was conducted as described in Example 8. The measured HA content was 1024 U, the virus was titer $10^{7.9}$ $CID_{50}/mL$.

Example 11: Culturing and Infection with Chemically Defined Media

Culturing of the cells occurred as described in Example 6, infection as described in Example 9. The total cell culture from culturing to harvesting of the infection therefore occurred in chemically defined medium.

Example 12: Culturing with Chemically Defined Media and Infection in Protein-Free Medium Culturing of the cells occurred as described in Example 6 in chemically defined medium, infection as described in Example 10 in protein-free medium.

Example 13: Culturing and Infection in Protein-Free Medium

Culturing of the cells occurred as described in Example 7, infection as described in Example 10. The entire cell culture from culturing to harvesting of the infection occurred in protein-free medium.

Example 14: General Description of Virus Purification

After conclusion of the virus multiplication phase, the cell culture harvest was filtered through a deep bed filter with a pore size of 0.45 or 0.5 μm in order to separate cells and cell fragments. As an alternative, this separation was conducted with a separator. The viruses contained in the clarified harvest were concentrated and purified, if necessary, by ultrafiltration, in which a membrane with an exclusion limit between 50,000 and 1,000,000, preferably 100,000 to 500,000, was used. The virus concentrate obtained was loaded on a chromatography column packed with CS (Cellufine Sulfate, Millipore). After contaminants were eliminated by washing with buffer, the viruses were eluted with a 0.3 to 3M NaCl solution. The eluate was desalted by ultrafiltration and further concentrated. As an alternative or in combination with chromatographic purification, an additional purification effect can be achieved by ultracentrifugation. Most viruses can also be purified according to their buoyant density by ultracentrifugation in a sucrose gradient with subsequent fractionation of the gradient. Virus inactivation with formaldehyde or β-propiolactone can be introduced at any point within the purification process, but preferably is used after concentration or after purification, since the volumes being inactivated are then already substantially reduced.

Example 15: Recovery of Inactivated Pure Virus Preparation for Formulation of Vaccines Flaviviruses (Central European encephalitis virus, strain K 23) were cultured according to Examples 5, 6 and 7 in different media at an inoculation dose of 0.2 MOI (for details, cf. Example 22).

The harvested, virus-containing culture medium was freed of any cell residues present by centrifugation and filtration via filters with a pore size of 0.45 μm. For safety reasons, this material was already inactivated after filtration by addition of β-propiolactone in a dilution of 1:2000 or 1:2500 and incubation at 2-8° C. for 24 h. A cell culture test of the inactivated preparations after 2 h of hydrolysis of the inactivation agent at 37° C. showed that no active virus was present up to a detection limit of less than 0.03 infectious units/mL.

For analysis of the subsequently described purification steps, a BCA [bicinchoninic acid] assay (Pierce) was used to determine the total protein content. The specific antigen content was determined with a sandwich ELISA using specific monoclonal antibodies against the E-glycoprotein (Niedrig et al., 1994, Acta Virologica 38:141-149) and a polyclonal antiserum produced in-house against purified virus from rabbits. The values for the inactivated starting material were then used as reference value (corresponding to 100%).

Purification by Gradient Centrifugation:

Inactivated virus preparations were purified according to known methods by density gradient ultracentrifugation (15-60% sucrose) at 80,000 G. The gradient was then fractionated and in samples of the fractions the extinction at 280 nm was determined to identify the virus peak. A sharp increase in extinction was found in the region of a sucrose concentration between 30 and 40% and the maximum was at 34 and 35%. From this region, the highest content of specific virus protein and the highest purity (determined as the ratio of virus protein to total protein) were also measured. Overall, more than 50% of the specific antigen content determined in the starting material was recovered in these peak fractions.

Chromatographic Purification:

The inactivated virus preparations (see above) were applied to a CS column that had been equilibrated beforehand with five column volumes of 50 mM phosphate buffer, pH 7.5. It was then washed with 10 column volumes phosphate buffer in order to eliminate unbound material. Bound material was then eluted with the same phosphate buffer with stagewise admixing of increasing amounts of the same buffer with addition of 3M NaCl. Between 3.2 and 3.9% of the specific antigen and 79 to 83% of the total protein was recovered analytically in the flow during application of the virus material. In the wash buffer, 6-11% of the total protein and 0-2.3% of the antigen were found. More than 95% of the antigen is therefore bound to the column material. During elution with 0.6 to 1.8M NaCl, about 60.0% of the antigen was recovered, the highest purity was achieved during elution with 1.2M NaCl. Higher salt concentrations to 3M NaCl eluted additional, small amounts (<15%) of antigen with lower specific purity.

Purification by Combination of Chromatography and Ultracentrifugation:

Combined eluate from chromatographic purification after 0.6 and 1.2M NaCl elution were subjected to ultracentrifugation for 2.5 h at 80,000 G as described above. The virus pellet was resuspended in 50 mM phosphate buffer pH 7.5 and analyzed. The total protein concentration of this preparation was reduced to 0.7% of the initial content and the degree of purity had been increased ten-fold by this step.

This virus preparation was subjected to gradient purification as described above. After fractionation a very similar gradient profile was found as achieved after direct gradient purification. The tip of the virus peak, however, had shifted slightly and now was at 37% sucrose.

Example 16: Recovery of a Virus Isolate and Virus Multiplication of a Human Herpes Virus By sterile puncture of a fresh herpes efflorescence in the blister stage (labial herpes blisters) with a tuberculin syringe, a minimal amount of tissue fluid was obtained and suspended according to Example 3 in standard medium with addition of antibiotics and filtered using a filter with a pore size of 0.45 μm. The filtrate was inoculated in a culture flask with a 25 cm² culture surface with adherent MDCK 33016 cells in standard medium and incubated at 37° C. After 4 days samples of the supernatant were taken and after 7 days the entire supernatant of the cultures were taken and frozen at less than −70° C. A sample taken after 4 days was diluted 1:10 and then in steps of 10 in standard medium containing 10 μg/mL trypsin; 100 μL of these dilutions were introduced to the MDCK 33016 cells in standard medium. After 13 days of incubation at 37° C., a CPE was found in a few cultures of the first dilution step. The supernatant of these cultures were harvested and diluted again and inoculated in new cultures. After 6 to 9 days an increasingly more distinct CPE was found in several dilution steps of this third virus passage as typical herpes virus plaques. A directly infected culture parallel with the same starting material with 175 cm² culture surface also showed exclusively the same typical plaques. For further cloning of the virus, this dilution process was repeated again, in which supernatant in cell cultures of the last positive dilution were used. In addition to harvesting of the culture supernatants, the remaining cells were fixed with a 3% formaldehyde solution for 16 h then incubated with 1% Triton X-100 for 30 min and then subjected to immunofluorescence investigations according to standard methods with specific, FITC-labeled monoclonal antibodies against HSV-1 (Biosoft product No. 17-088). It was found that only cells in the vicinity of the plaque had immunofluorescence. By this demonstration and by a specific PCR demonstration, the isolate was clearly identified as herpes simplex virus 1.

The cloned virus was further multiplied in standard medium in suspension cultures and used for production seed virus at a sufficient virus titer (>$10^6$ infectious units/mL) as described in Example 3. The seed virus preparations regularly contained virus titers between $10^7$ and $10^8$ $CID_{50}$/mL. Determination of the virus titer occurred according to standard methods known to one skilled in the art in HEP-2 or Vero cells, but can also occur in adherent MDCK cells in which evaluation of the titrations is carried out with reference to typical plaques. The seed virus preparations were aliquoted at −70° C. or frozen below that and used for infection of production cells. The possibility of using the same MDCK cells and the same culture conditions in terms of media and additives as for later production is a significant advantage, since the documentation demands during registration of the corresponding products are significantly reduced and acceptance of the seed virus is improved.

Example 17: Production of Human Herpes Viruses

For infection of the production cells according to Examples 8 to 13 with herpes simplex virus 1 (isolate as described in the preceding example), a MOI of 0.1 or 0.01 and an incubation time of 48 to 96 h after harvest are chosen. However, lower or higher MOIs with correspondingly longer or shorter incubation times can also be used, in which the yields could vary somewhat since the optimal harvesting time is not always found. As a rule, however, the aforementioned conditions are preferred, so that culture yields for economic reasons and for facilitation of subsequent workup do not lie significantly below $10^8$ 50% culture-infectious units/mL ($CID_{50}$/mL). Beyond this, this time scheme can be favorably adapted in normal work rhythms. Unduly low MOIs below 0.0001 and lengthened incubation times almost always lead to lower yields and are therefore suboptimal.

Example 18: Multiplication of Animal Herpes Viruses

Herpes virus suis (pseudorabies virus), "Phylaxia" strain (vaccine strain) was inoculated for infection of a production culture on a small scale with 100 mL spinner cultures according to Example 1. Infection of the production culture occurred at a cell count of 1×$10^6$ cells/mL with a MOI of 0.01; harvesting of the infectious culture supernatant occurred after an incubation time of 3 to 5 days at 37° C. or at 33° C. The yields to be expected were in the range of or significantly higher than $10^8$ infectious units/mL. Comparably high titers could be achieved at different incubation temperatures:
  after 3 days at 37° C.: $10^{8.7}$ $CID_{50}$/mL,
  after 3 days at 33° C.: $10^{8.6}$ $CID_{50}$/mL,
  after 5 days at 37° C.: $10^{7.9}$ $CID_{50}$/mL,
  after 5 days at 37° C.: $10^{8.3}$ $CID_{50}$/mL.

The titration of the viruses was conducted in these cases in CRFK (Crandall feline kidney) cells and after 7 days interpreted with reference to the cytopathic effect.

Example 19: Multiplication of Animal Adenoviruses

Adenovirus (canine adenovirus 1, CAV-1 vaccine strain 269) was inoculated for infection of a production culture on small scale in 100 mL spinner cultures according to Example 1. Infection of the production culture occurred in a cell count of 1 to 1.5×$10^6$ cells/mL with a MOI of 0.01, harvesting of the infectious culture supernatant after an incubation time of 3 or 5 days at 37° C. or at 33° C. Regardless of the incubation temperature (33 or 37° C.) and duration of the infection phase (3 or 5 days), almost identical titers of $10^{7.5}$ or $10^{7.6}$ $CID_{50}$/mL were found in t harvest.

Yield determination with reference to virus titer occurred by titration in adherent MDCK 33016 cells in microtiter plates (see Example 2) and was evaluated 7 days after preparation by means of CPE. The infected cultures of the titration were kept in an EME [sic] medium with addition of 2% bicarbonate (from a 5% stock solution) but without serum or protein addition. This titration system proved to be a sensitive detection system, since it still multiplies the adenovirus very efficiently even in the smallest diluted amounts (recognizable in the titer values achieved).

Additional infection lots demonstrate the superiority of the suspension culture system relative to an adherent culture lot of the same type.

Adherent MDCK 33016 cultures were cultured in Falcon culture flasks (175 cm$^2$) to confluence of the culture and infected with CAV-1 on achievement of confluence. The same amounts (MOI=0.01) of the same virus preparation was used for infection which was also used for infection of parallel cultivated suspension cultures. Bulk cultures were cultured in the same medium (standard medium) and switched at the time of infection by a medium exchange to supplement-free medium. Both culture systems were incubated at 37° C. and the culture supernatant harvested 5 days after infection. Cell-free culture supernatants were titrated as described above in MDCK cells. The virus yield of the adherent system amounted to $10^{6.3}$ CID$_{50}$/mL, that of the suspension culture lot $10^{7.8}$ CID$_{50}$/mL, i.e., about 30 times more.

Example 20: Multiplication of Paramyxoviruses

In almost identical fashion as in the previous example for adenoviruses, a representative of the paramyxoviruses were used (ATCC, strain VR-288). The harvesting time point after only 3 days was a deviation, since this virus replicates very rapidly and evaluation and titration also occurred sooner, namely after 5 days. Cultures that were further incubated after infection at 37° C. gave yields of $10^{7.4}$ CID$_{50}$/mL; the same titers were measured when the infection temperature was reduced to 33° C. from the infection point.

Similarly to adenovirus, MDCK 33016 cells also proved to be a very appropriate titration system for the paramyxovirus with efficient virus replication in MEM medium with serum or protein addition (bicarbonate addition also occurred here). As described in the example for adenoviruses, a direct comparison between adherent and suspension cultures was also conducted here. The maximum yield in the adherent system was $10^{6.6}$ CID$_{50}$/mL after 96 h of infection time, the suspension culture system gave in comparison much better and more rapid yields of $10^{7.3}$ CID$_{50}$/mL after 72 h.

As an alternative, adherent MDCK 33016 cells according to Example 2 were infected with MEM with 5% FCS with another virus of the same family (PI-3, ATCC VR-93). After 1 week of incubation at 37° C., the supernatants contained at least $10^6$ CID$_{50}$/mL after titration in CV-1 cells (ECACC 87032605), showed a positive hemagglutination with guinea pig erythrocytes and a positive immunofluorescence with specific antibodies (anti-PI-3 MAb-FITC from the Biosoft Co.).

The same virus strain (PI-3, ATCC VR-93) was also used under chemically defined and protein-free media in similar fashion to Example 12 for infection in MDCK 33016 cultures. On the infection days 3, 5, 9 and 12, 22% of the culture volume was removed and replaced by fresh medium. On day 7, 50% of the culture volume including the cells was removed and replaced with new medium. Overall the culture volume during infection was completely exchanged more than once and offered the opportunity by medium supplementation to further multiply the cells according to the dilution. The method employed corresponds overall to a roughly 1:2.4 passage of the culture in which only the excess amounts were removed. The significantly higher passage or dilution of the culture, possible especially in the initial phase, was not fully exploited here by far.

The following virus yields were measured.

| | Day of infection: | | | | | |
|---|---|---|---|---|---|---|
| | 3 | 5 | 7 | 9 | 12 | 14 |
| log CID$_{50}$/mL: | 7.9 | 8.05 | 8.25 | 7.45 | 6.7 | 7.0 |

(average values from duplicate tests)

Example 21: Multiplication of Reoviruses

Suspension cultures of MDCK 33016 cells in standard medium were infected with reovirus type 3 (obtained from Bio Doc, Hannover) at a MOI of 0.01 and further incubated for 3 or 5 days at 33 or 37° C. Samples of the culture supernatants were taken after 5 and 7 days and titrated in the system furnished using BHK cells in MEM medium with 3% FCS. Evaluation of the titrations occurred after 7 days.

The virus yields of the suspension cultures after 5 days at 37° C. were $10^{8.1}$ CID$_{50}$/mL, at 33° C. $10^{8.0}$ CID$_{50}$/mL. After 7 days the titers in both temperature lots were at $10^{8.0}$ CID$_{50}$/mL.

The same virus strain was used in chemically defined and protein-free media similar to Example 12 in MDCK 33016 cultures for infection at a MOI of 0.01. On the infection days 3, 7 and 10, 22% of the culture volume was removed and replaced by fresh medium. On day 7, 50% of the culture volume including the cells was removed and replaced with new medium. Overall the culture volume during infection was therefore almost completely exchanged and offered the cells an opportunity by medium supplementation to further multiply according to the dilution. The method employed corresponds to a roughly 1:2 passage of the culture in which only the excess amounts were removed. The significantly higher passage or dilution of the culture, possible especially in the initial phase, was not fully exploited here by far.

The following virus yields were measured.

| | Day of infection: | | | |
|---|---|---|---|---|
| | 3 | 7 | 10 | 14 |
| log CID$_{50}$/mL: | 5.4 | 7.1 | 6.6 | 6.6 |

(average values from duplicate tests)

Example 22: Multiplication of Flaviviruses

Suspension cultures of MDCK 33016 cells with a cell density of 1-1.5×$10^6$ cells/mL were infected under standard conditions (standard medium 37° C. culture and infection temperature) with a Central European encephalitis virus (strain K23, Niedrig et al., 1994, Acta Virologica 38:141-149). Deviating from the previous examples, strongly varying MOIs were used for infection. Moreover, the infection cultures were partly kept in chemically defined medium or in medium without protein-containing additives. Different culture and harvesting methods were used which show that, even when different parameters are changed, high yields can be achieved with the system and even multiple harvests are possible. These changes are summarized in Table 3. Virus titration occurred in A 549 cells (ECACC No. 86012804) and was evaluated after 5 days with reference to CPE. The fact that the repeated harvest of the same culture was accompanied by exchange of the culture medium so that the cells during each harvest were supplied with new medium and could therefore grow further is worth noting. Without these harvests, the culture would not remain viable and productive over a longer period. Since frequent medium exchanges at short intervals could not compensate for the high metabolic output of the cultures, additional medium supplements and increases of the cultures occurred after 4 or 5 days of infection time.

specific antibody as a deviation (designation F 86012, kindly furnished by Dade Behring). Product No. 39015 (Sigma Co.) was used as anti-human IgG antibody with biotin labeling. The specific detection of active virus multiplication with this system yields brownish-pink colored cells that are easy to recognize on low magnification in a microscope. Virus-negative cells on the other hand appear uncolored or have only a slight coloration. Virus titrations at 3 weeks after

TABLE 3

Multiplication of CEE virus/K23 in MDCK 33016 cultures in standard medium and in alternative media using different MOI and harvesting variants.

| MOI | Yield (log 10 $CID_{50}/mL$) during harvest after __ days Medium | | | | | | | | Medium employed |
|---|---|---|---|---|---|---|---|---|---|
| | 1 | 2 | 3 | 4 | 5 | 6 | 7 | 8 | |
| Lots with multiple harvests during complete media exchange | | | | | | | | | |
| 2.0 | 9.0 | | 8.8 | | | | | 8.8 | Standard medium |
| 2.0 | | 9.0 | | (M + 30)+ | | | | 8.4 | Standard medium |
| 2.0 | | 6.1 | | (M + 30) | | | | 6.1 | Protein-free medium |
| 0.2 | | 7.8 | | (M + 30) | | | | 7.8 | Chemically |
| 0.2 | 8.7 | | 8.0 | | | | | 7.7 | defined medium |
| 0.2 | 8.3 | | (M + 30) | 8.6 | | | | | Standard medium |
| 0.2 | | 9.0 | | (M + 30) | 9.0 | | | | Standard medium |
| 0.2 | 8.6 | | 9.2 | | | | 9.0 | | Standard medium |
| 0.2 | 9.0 | | | | 9.0 | | | 8.6 | Standard medium |
| 0.2 | | 7.3 | | (M + 30) | 8.2 | | | | Standard medium |
| 0.2 | | 7.2 | | (M + 30) | 8.6 | | | | Protein-free medium Chemically defined medium |
| Lots with sampling without media exchange or suplementation | | | | | | | | | |
| $10^{-0.3}$ (=−0.5) | 7.7 | 8.3 | 9.2 | 9.4 | 9.3 | | | | Standard medium |
| $10^{-0.3}$ | 6.3 | 7.5 | 8.4 | 8.6 | 8.9 | | | | Medium MEM, adherent culture, 1% ECS |
| $10^{-1.3}$ (=−0.05) | 5.2 | 6.3 | 6.6 | 6.8 | 6.8 | | | | Standard medium, temperature exceeded by agitator |
| $10^{-1.3}$ | 5.1 | 6.2 | 7.1 | 8.0 | 8.4 | | | | Standard medium |
| $10^{-2.3}$ | 4.8 | 6.2 | 7.6 | 7.5 | 8.1 | | | | Standard medium |
| $10^{-3.3}$ | 3.4 | 4.7 | 4.9 | 5.6 | 6.0 | | | | Standard medium |
| $10^{-4.3}$ | 2.7 | 3.7 | 4.3 | 4.3 | 4.4 | | | | Standard medium |
| $10^{-5.3}$ | 2.5 | 2.6 | 3.4 | 3.7 | 4.3 | | | | Standard medium |

+(M + 30) means medium supplementation + 30% of the culture volume on the stated day Example 23: Multiplication of Picornaviruses Adherent MDCK 33016 cultures were cultured for infection with hepatitis A virus (HAV, strain HM 175, ATCC VR-1358) in MEM medium with addition of 5% fetal calf serum and bicarbonate (cf. example 2). In the context of the experiment, an additional "Munich" virus isolate was used (cf. Frosner et al., 1979, Infection 7:303-305). The diluted virus was inoculated into the freshly prepared culture and the culture incubated at 37° C. The cultures were subjected to further passage of 1:4 in alternating rotations of 3 to 4 days.

Suspension cultures of MDCK 33016 cells were cultured in standard medium according to Example 1, inoculated with HM 175 and incubated at 33° C. and then subjected to 1:10 passage weekly. The adherent cells in suspension cultures were further maintained after infection for up to 35 days. Detection of the active virus replication then occurred by means of CPE (strain HM 175) or according to an already described method (see Virus titration, 93 in Gregersen et al., 1988; Med. Microbiol. Immunol. 177:91-100). A human anti-HAV antibody as purified IgG was used as virus-preparation were also evaluated with the same detection methods, for which human diploid cells (MRC-5) were used as the culture system.

In all the infection lots described above and with both virus isolates employed, an active HAV replication can be detected in the MDCK cells. A surprisingly rapid virus multiplication was detected with strain HM 175 in suspension cultures. On day 7 after infection, the measured virus titer in the supernatant was $10^{5.4}$ $CID_{50}/mL$; this culture was subjected to 1:10 passage weekly by simple dilution and again yielded similar virus titers in the resulting cultures after 7 days. At the end of culturing and after two additional cell passages, the virus titer in one sample of the cell-free medium was determined. A sample of the entire culture was also taken and the cells contained in it broken down by two-fold freezing at −20° C. and thawing. The cell components were removed by centrifugation before the samples were titrated. The virus yields obtained from this lot are summarized in Table 4 and show that, without an adverse effect on specific yields, a weekly ten-fold multiplication of the cultures is possible, in which good virus titers per volume unit can be harvested despite the massive amount increase. It is worth noting that a significant fraction of virus is then found in the supernatant, which is also surprising for this strongly cell-bound virus (see Table 4).

TABLE 4

Multiplication of hepatitis A virus (strain HM 175) in MDCK 33016 suspension cultures with continuous multiplication and increase in the culture volume.

| Day after infection | Cell passage (increase in culture volume) | Relative harvest volume (day 0 = 1) | Total virus yield ($CID_{50}$) | |
|---|---|---|---|---|
| | | | In medium | After cell breakdown |
| 7 | 1:10 | 1 | $10^{7.4}$ | $10^{7.8}$ |
| 14 | 1:10 | 10 | $10^{8.5}$ | $10^{9.2}$ |
| 21 | 1:10 | 100 | n.d. | n.d. |
| 28 | 1:10 | 1000 | $10^{10.8}$ | $10^{11.4}$ |
| 35 | End | 10,000 | $10^{12.5}$ | $10^{14.2}$ | n.d.: not determined

Example 24: Multiplication of Pneumoviruses

Adherent MDCK 33016 cultures in MEM medium with addition of 5% FCS and bicarbonate (cf. Example 2) were used for infection with human RSV-A (strain A-2; ATCC VR-1302). The virus was diluted 1:100 and inoculated into the freshly prepared culture and the culture then incubated at 37° C. After a week 1 mL of the culture supernatant was transferred to a new culture and again incubated for 7 days. The harvested culture supernatant in MA-104 cells (ECACC 85102918), when titrated, shows during evaluation of the titration a virus titer of $10^{5.5}$ $CID_{50}$/mL by means of CPE.

The virus strain A-2, ATCC VR-1302 was used for infection under chemically defined and protein-free media similar to Example 12 in MDCK-33016 cultures. On infection days 3, 5, 7, 9 and 12, 22% of the culture volume was taken and replaced by fresh medium. On day 7, 50% of the culture volume including the cells was removed and replaced by new medium. In all, the culture volume during infection was exchanged completely more than once and gave the cells an opportunity by medium supplementation to further multiply according to the dilution. The method employed corresponds overall to a roughly 1:2.4 passage of the culture in which only the excess amounts were removed. The significantly higher passage or dilution of the cultures possible, especially in the initial phase, was not fully exploited here by far.

The following virus yields were measured:

| | Day of infection: | | | | | |
|---|---|---|---|---|---|---|
| | 3 | 5 | 7 | 9 | 12 | 14 |
| log $CID_{50}$/mL: | 7.85 | 8.5 | 7.55 | 6.55 | 4.45 | n.t. |

(average values from duplicate tests)
n.t.: Samples not tested, since non-sterile The virus strain RSV-B, ATCC VR-1401 was tested in an equivalent lot. For virus titration Hep-2 cells (subline Hep-2C, kindly furnished by the Paul Ehrlich Institute, formerly of Frankfurt) was used, since the typical viral syncytia are better developed in it and evaluation is therefore facilitated. The following virus yields were measured:

| | Day of infection: | | | | | |
|---|---|---|---|---|---|---|
| | 3 | 5 | 7 | 9 | 12 | 14 |
| log $CID_{50}$/mL: | 3.7 | 4.75 | 7.45 | 6.3 | 3.2 | 3.75 |

(average values from duplicate tests)

Example 25: Multiplication of Rotaviruses

Adherent MDCK 33016 cultures in MEM medium with addition of 5% supplement and bicarbonate (cf. Example 2) were used for infection with simian rotavirus SA-11 (ATCC, VR-899). The virus was inoculated 1:100 in the freshly prepared culture and is supplemented with trypsin (0.5-10 µg/mL, preferably 5 µg/mL) and the culture then incubated at 37° C. The cultures were again passaged 1:4 in alternating 3-4-day rotations.

Samples of the culture after trypsinization were frozen three times in succession (–20° C.) and thawed again and then used for virus titration. Virus titration occurs in MA-104 cells (ECACC 85102918). Evaluation of titration occurs after 10 days by means of CPE. Optimal virus titers are found in this virus only after 5 to 10 cell passages, depending on the virus content on the initial material.

Selection of the initial material for seed virus production then occurs, which is prepared similar to the procedure described in Example 3. The seed virus is then used for production as described in Examples 8, 9 and 10, in which the trypsin concentrations stated there are maintained for the different media.

Samples of the culture after trypsinization are frozen three times in succession (–20° C.) and thawed again and then used for virus titration. Virus titration occurs in MA-104 cells (ECACC 85102918). Evaluation of titration occurs after 10 days by means of CPE. Optimal virus titers are found in this virus only after 5 to 10 cell passages, depending on the virus content on the initial material.

Selection of the initial material for seed virus production then occurs, which is prepared similar to the procedure described in Example 3. The seed virus is then used for production as described in Examples 8, 9 and 10, in which the trypsin concentrations stated there are maintained for the different media.

According to additional experiences, a somewhat different path was taken that led to better results. Initially the trypsin concentration employed was further optimized by tests in MA-104 cells and then set at 8-20 µg/mL. EDTA concentrations between 1.6 and 4.4 µg/mL (1.6 at 8 µg/mL trypsin or 4.4 at 20 µg/mL trypsin) were also supplemented. The virus from these optimized conditions was titrated as described above, but with increased trypsin concentrations (8 or 16 µg/mL) and in the presence of EDTA and yielded optimal titers already after only 5 days during interpretation of the cultures. Virus that was recovered under these optimized conditions was inoculated into serum-free medium after adjustment of the infection dose to a MOI of 0.1 or 0.01 in MDCK 33016 suspension cells (similar to Example 5 but in a 100 mL scale, 8 µg/mL trypsin, 1.6 µg/mL EDTA). The supernatant virus titer of these cultures after 1 day of incubation at 37° C. was $10^{6.0}$ or $10^{6.1}$ $CID_{50}$/mL, after 2 days $10^{7.6}$ or $10^{6.4}$ $CID_{50}$/mL. At 20 µg/mL trypsin and 4.4 µg/mL EDTA, titers between $10^{5.8}$ and $10^{6.0}$ $CID_{50}$/mL were found after 1 to 3 days.

Two additional passages with the samples harvested on day 2 gave maximum titers of $10^{7.5}$ or $10^{7.9}$ $CID_{50}$/mL at a MOI of 0.01 and 8 µg/mL trypsin/1.6 µg/mL EDTA so that a certain adaptation presumably had occurred, which, however, required only a few virus passages in these cultures.

Example 26: Multiplication of Vaccinia Viruses

Adherent MDCK 33016 cultures in MEM medium with addition of 5% FCS and bicarbonate (cf. Example 2) are used for infection with vaccinia virus (strain WR, ATCC VR-119). The virus is inoculated in the freshly prepared culture and the culture then incubated at 37° C. After 5 days a sample of the harvested culture supernatant is used for virus titration.

Suspension cultures of MDCK 33016 cells are cultured in standard medium according to Example 1 and inoculated with vaccinia virus at 1:1000 dilution. On further incubation of the infected culture, samples are taken at two-day intervals and titrated.

Virus titration occurs in Vero cells (WHO seed, obtained from ECACC). Evaluation of titration occurs by means of CPE after 5 days. Virus titers above $10^6$ $CID_{50}$/mL are found at a MOI of 0.01 already after 2 to 3 days.

Example 27: Multiplication of Rhabdoviruses

Suspension cultures in standard medium according to Example 1 were seeded in cell culture flasks with a cell density of $1 \times 10^6$ cells per mL of medium. After growing the cultures, two cultures were infected with a rabies virus (strain Pitman-Moore, vaccine virus strain) with a MOI of 0.01 and one culture of MOI of 0.001. The cultures were incubated at 37° C. and detached every 4 or 3 days with trypsin and subjected to passages in a 1:10 ratio (after 4 days) or 1:8 ratio (after 3 days) and maintained this way for 18 days (see Table 5). The infection success was followed at each passage. A culture was provided with 3.5% formalin solution and incubated for 3 days at room temperature in the solution in order to achieve inactivation of the viruses. After elimination of the formalin solution, the culture was washed with PBS and incubated for 25 min with 1% Triton X100 in PBS at room temperature. After removal of the solution, it was washed three times with PBS and an FITC-labeled antibody against rabies virus was applied (50 µL 1:400 diluted rabbit antirabies IgG FITC, Dade Behring, OSHY 005). After 90 min of incubation at 37° C., it was washed again with PBS and the culture evaluated under an inverted fluorescence microscope.

As an alternative, virus titrations of the culture supernatants were conducted according to standard methods in MRC-5 cells, which were also evaluated by immunofluorescence as described above after formalin/Triton pretreatment. By means of the virus titers achieved with this system, a rough correlation to the yield in the corresponding production methods was made using MRC-5 cultures for an approved human vaccine (Rabivac), which permits an orientation as to how much vaccine antigen is contained per mL of culture harvest (see Table 5).

After only 4 days both lots (MOI 0.01 and 0.001) showed positive results and then a similar infectious course, but at the lower MOI the infectious course—recognizable in the virus titers that were lower up to day 11 at about 1.2 to 0.5 log $CID_{50}$—were slightly slowed. From the third passage of the cultures on day 11, a very intense specific immunofluorescence with incipient cell destruction was found in all cultures, which then further increased until most of the cells have been fully destroyed by the fifth passage on day 18 so that the infection was terminated. The content of specific virus continuously rose to day 14 to then diminish again as a result of increasing cell destruction. The results of this infectious course are summarized in the following table and show that (measured on the known slow virus multiplication of rabies viruses) a very rapid virus multiplication without adaptation is be expected in these cells, in which good antigen yields can be harvested despite continuing remultiplication of the cells at regular intervals and repeatedly.

TABLE 5

Multiplication of rabies virus in MDCK 33016 cultures during continuous enlargement of the culture volume.

| Day after infection | Passage of the cells | Relative culture volume | Rabies antigen (vaccine doses/mL) |
|---|---|---|---|
| 4 | 1:4 | 1 | not determined |
| 7 | 1:3 | 4 | not determined |
| 11 | 1:4 | 12 | 0.2-0.4 |
| 14 | 1:3 | 36 | 0.4-0.5 |
| 18 | not applicable | 108 | 0.4-0.5 |

In similar fashion the same virus was directly inoculated in suspension cultures according to Example 1 in which a MOI of 0.0001 was additionally used. Standard medium was exclusively used again for the entire infectious course and the cultures were also transferred twice weekly at 1:8 or 1:10. Transfer occurred only by simple dilution of the cells in fresh medium and seeding anew. The infection success was followed here only with reference to virus titration in MRC-5 cells as described above. The infections at all three MOIs after only 4 days yielded positive virus titers in the culture supernatant. The virus titers rose after initial dilution loss after the seventh day from passage to passage and despite the again conducted exponential dilution continuously rose but led to no massive cell destruction in the suspension cultures. The infection was followed to the eighth passage (day 28 after infection) and then interrupted.

Virus samples from these infections were frozen as seed virus and used for a new infection of suspension cultures beginning with 100 mL and also in the standard medium and under the same passage conditions as described above. The MOI was reduced in this case to 0.000025. The infection was maintained over six cell passages (21 days). Virus titers which, converted, gave about 0.3 vaccine doses per mL of culture supernatant were measured at the end of this infectious course with slowly rising virus titers despite the massive passage dilutions. If the entire culture volume and not just a part of it had been subjected to further passages, about 500 L of culture could have been harvested after six passages, which would have been a virus yield corresponding to about 150,000 vaccine doses.

Example 28: Multiplication of Togaviruses

Adherent MDCK 33016 cultures in standard medium or in EME with addition of 5% FCS and bicarbonate (cf. Example 2) were used for infection with Japanese encephalitis virus (ATCC VR-343). The virus was diluted with a MOI from 0.1 to 0.001 and inoculated in a freshly prepared culture and the culture then incubated at 33° C. or alternatively at 37° C. The active virus multiplication was determined by means of immunofluorescence with specific antiserum in acetone-fixed cells and, depending on the MOI employed, the time of maximum virus antigen presence was determined. Virus titration of virus harvests from a supernatant occurred in Vero cells and was also evaluated by immunofluorescence. As an alternative to immunofluorescence, an avidin-biotin peroxidase system can be used for virus detection and for evaluation of the titrations similar to Example 23 (multiplication of picornaviruses described for hepatitis A virus).

The invention claimed is:

1. A method for production of a virus or a protein produced from the virus for use in manufacture of a viral vaccine on a commercial scale, comprising:
   (a) increasing the volume of a suspension culture of Madin-Darby Canine Kidney (MDCK) cells in a serum-free medium, a protein-free medium, or a chemically defined medium, in a fed-batch system by diluting with fresh medium to the suspension culture to increase its volume to at least 1000 L without removal of the original medium, wherein the fresh medium is added to the original medium to increase the volume of the suspension culture to the at least 1000 L such that the dilution is 1:10 to 1:2 original medium to fresh medium,
   (b) infecting the MDCK cells in the at least 1000 L volume with the virus,
   (c) propagating the viruses in the MDCK suspension culture, and
   (d) isolating the viruses or a protein produced from the viruses from the cell culture, wherein the virus is selected from the group consisting of an adenovirus, orthomyxovirus, paramyxovirus, reovirus, picornavirus, enterovirus, flavivirus, herpes virus and pox virus.

2. The method according to claim 1, wherein the MDCK cells in the suspension culture originate from the cell line MDCK 33016.

3. The method according to claim 1 or 2, wherein the virus selected is a dsDNA, RNA(+), or RNA(−) virus and is an adenovirus, orthomyxovirus, paramyxovirus, reovirus, picornavirus, enterovirus, flavivirus, herpes virus or pox virus.

4. The method according to claim 1 or 2, wherein the cells are cultured in a chemically defined medium before infection and in a protein free medium after infection.

5. The method according to claim 1 or 2, further comprising purifying the virus by Cellufine Sulfate (CS) chromatography and/or ultracentrifugation in a sucrose gradient.

6. The method of claim 1 or 2, wherein the vaccine is mixed with an appropriate adjuvant, auxiliary, buffer, diluent or drug carrier.

7. A method for production of a virus or a protein produced from the virus for use in manufacture of a viral vaccine on a commercial scale, comprising:
   (a) increasing the volume of a suspension culture of Madin-Darby Canine Kidney (MDCK) cells in a serum-free medium, a protein-free medium, or a chemically defined medium, in a fed-batch system by diluting with fresh medium to the suspension culture to increase its volume to at least 1000 L without removal of the original medium, wherein the fresh medium is added to the original medium to increase the volume of the suspension culture to the at least 1000 L such that the dilution is 1:10 to 1:2 original medium to fresh medium,
   (b) infecting the MDCK cells in the at least 1000 L volume with the virus,
   (c) propagating the viruses in the MDCK suspension culture, and
   (d) isolating the viruses or a protein produced from the viruses from the cell culture, wherein the virus is an influenza virus and the influenza virus used in step (b) is from a primary isolate that was pre-multiplied in cell culture to produce a pure isolate.

* * * * *